(12) United States Patent
Weiner et al.

(10) Patent No.: US 8,227,487 B2
(45) Date of Patent: *Jul. 24, 2012

(54) SELECTIVE SEROTONIN 2A/2C RECEPTOR INVERSE AGONISTS AS THERAPEUTICS FOR NEURODEGENERATIVE DISEASES

(75) Inventors: David M. Weiner, San Diego, CA (US); Robert E. Davis, San Diego, CA (US); Mark R. Brann, Rye, NH (US); Carl-Magnus A. Andersson, Hjärup (SE); Allan K. Uldam, Vaerloese (DE)

(73) Assignee: ACADIA Pharmaceuticals Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/169,893

(22) Filed: Jun. 27, 2011

(65) Prior Publication Data

US 2011/0257229 A1 Oct. 20, 2011

Related U.S. Application Data

(60) Continuation of application No. 12/759,662, filed on Apr. 13, 2010, now Pat. No. 7,994,193, which is a continuation of application No. 11/416,527, filed on May 3, 2006, now Pat. No. 7,732,462, which is a division of application No. 10/759,561, filed on Jan. 15, 2004, now Pat. No. 7,601,740.

(60) Provisional application No. 60/441,406, filed on Jan. 16, 2003, provisional application No. 60/479,346, filed on Jun. 17, 2003.

(51) Int. Cl.
*A61K 31/47* (2006.01)
*A61K 31/445* (2006.01)
(52) U.S. Cl. ........................................ 514/310; 514/317
(58) Field of Classification Search .................. 514/310, 514/317
See application file for complete search history.

(56) References Cited

U.S. PATENT DOCUMENTS

| | | | |
|---|---|---|---|
| 5,837,730 A * | 11/1998 | Javitt | 514/551 |
| 7,732,462 B2 * | 6/2010 | Weiner et al. | 514/310 |
| 7,994,193 B2 * | 8/2011 | Weiner et al. | 514/310 |

* cited by examiner

*Primary Examiner* — Jennifer M Kim
(74) *Attorney, Agent, or Firm* — Jones Day

(57) ABSTRACT

Behavioral pharmacological data with the compound of formula (I), a novel and selective 5HT2A/2C receptor inverse agonist, demonstrate in vivo efficacy in models of psychosis and dyskinesias. This includes activity in reversing MK-801 induced locomotor behaviors, suggesting that this compound may be an efficacious anti-psychotic, and activity in an MPTP primate model of dyskinesias, suggesting efficacy as an anti-dyskinesia agent. These data support the hypothesis that 5HT2A/2C receptor inverse agonism may confer antipsychotic and anti-dyskinetic efficacy in humans, and indicate a use of the compound of formula (I) and related agents as novel therapeutics for Parkinson's Disease, related human neurodegenerative diseases, and psychosis.

12 Claims, 3 Drawing Sheets

US 8,227,487 B2

SELECTIVE SEROTONIN 2A/2C RECEPTOR INVERSE AGONISTS AS THERAPEUTICS FOR NEURODEGENERATIVE DISEASES

RELATED APPLICATIONS

This application is a continuation of U.S. application Ser. No. 12/759,662, filed Apr. 13, 2010, now U.S. Pat. No. 7,994,193 which is a continuation of U.S. application Ser. No. 11/416,527, filed May 3, 2006, now U.S. Pat. No. 7,732,462 which is a divisional of U.S. application Ser. No. 10/759,561, filed Jan. 15, 2004, now U.S. Pat. No. 7,601,740 which claims priority to U.S. Application No. 60/441,406, filed Jan. 16, 2003, and U.S. Application No. 60/479,346, filed Jun. 17, 2003, all of which are incorporated by reference in their entireties.

FIELD OF THE INVENTION

The present invention relates to the therapeutic use of N-(1-methylpiperidin-4-yl)-N-(4-fluorophenylmethyl)-N'-(4-(2-methylpropyloxy)phenylmethyl)carbamide and related serotonin 2A/2C receptor inverse agonists to treat a variety of human neurodegenerative diseases including Parkinson's Disease, Huntington's Disease, Lewy Body Dementia, and Alzheimer's Disease. Specifically, these agents improve motor function in Parkinson's Disease, and Huntington's Disease. Specifically, N-(1-methylpiperidin-4-yl)-N-(4-fluorophenylmethyl)-N'-(4-(2-methylpropyloxy)phenylmethyl) carbamide and related compounds can be used to control the behavioral and neuropsychiatric manifestations present in all of these disease states. Pharmaceutical compositions comprised of a combination of N-(1-methylpiperidin-4-yl)-N-(4-fluorophenylmethyl)-N'-(4-(2-methylpropyloxy)phenylmethyl)carbamide and existing therapeutic agents are also disclosed.

BACKGROUND OF THE INVENTION

Neurodegenerative disorders (NDs) are a group of related human maladies that share a common pathophysiological feature, the progressive degeneration of selective neuronal populations over the course of time. These neurodegenerative diseases include but are not limited to Alzheimer's Disease and related dementias, Parkinson's Disease, Huntington's Disease, Lewy Body Disease and related movement disorders, and Friedrich's Ataxia and related Spinocerebellar Ataxia's. Each of these disorders has unique clinical aspects including age of onset, time course of progression, neurological signs and symptoms, neuropsychiatric symptoms, and sensitivity to known therapeutic agents. In addition, the pathophysiological basis of each of these disorders is caused by genetic mechanisms unique to each disease.

Despite significant progress in elucidating the genetic causes underlying these disparate disorders, relatively little is known about the biochemical mechanisms that cause the selective neuronal degeneration common to all of them. In addition, for the most common of these disorders, including Parkinson's Disease and Alzheimer's Disease, the genetic factors that cause the rare familial forms of these diseases have been discovered, but the pathophysiological basis of the vast majority of sporadic cases is still unknown. Because of this, no specific therapeutic agents currently exist that can directly modify disease progression. Instead, clinicians utilize a variety of existing agents to provide symptomatic relief of the motor, cognitive, and neuropsychiatric manifestations that characterize these disorders. None of these existing agents were designed and developed to specifically treat patients with NDs.

Of the various neurological symptoms that characterize the NDs, abnormalities of motor function, including bradykinesias, dyskinesias and chorea, and the emergence of neuropsychiatric symptoms, including psychosis, and affective symptoms such as anxiety and depression, are common and severely impact upon the patient's functional status and quality of life. Unfortunately, most existing therapeutic agents, including antipsychotics and antidepressants, often demonstrate efficacy, yet are very poorly tolerated in these patients. In addition, the available therapeutic agents for Parkinson's Disease, including L-dopa and dopamine agonists, while generally effective, cause the emergence of severe treatment-limiting side effects that are currently intractable to pharmacotherapy.

Multiple factors, both disease and drug related, are primarily responsible for the limited tolerability of these agents. First, patients with neurodegenerative disease are particularly sensitive to most therapeutic agents that are designed to cross the blood-brain barrier and interact with neuronal targets that confer efficacy against adverse motoric or neuropsychiatric symptoms. For instance, atypical antipsychotics are generally well tolerated by healthy volunteers, or in patients with primary psychiatric disorders like schizophrenia; brain states that are not characterized by neuronal degeneration. In contrast, when these agents are administered to patients with Parkinson's or Huntington's Disease, they display severe, treatment-limiting adverse effects on motor function, cause severe sedation, and can worsen cognitive functioning. The direct effects of the neuronal loss characteristic of NDs, and the adaptive changes that occur secondarily to this are bath posited to create a neurochemical and/or neurophysiological state in ND patients that confer this extra sensitivity.

Second, the known mechanisms of action of these drugs, including antagonism of dopamine receptors, is not tolerated in some patient populations secondary to specific alterations in distinct neuronal systems. For instance, Parkinson's patients have a relatively selective degeneration of the ascending dopaminergic neuronal systems, and as a consequence of this they are deficient in central dopamine neurotransmission. It is therefore not surprising that drugs that further attenuate dopaminergic neurotransmission, by blocking dopamine receptors, are not well tolerated.

Lastly, nearly all presently known therapeutic agents lack specificity in their mechanisms of action. Antipsychotic and antidepressant drugs possess a multitude of pharmacologically relevant interactions with critical neuronal proteins including a host of cell surface receptors, ion channels, and re-uptake transporters. This lack of drug target specificity is known to confer a variety of adverse effects in non-ND patient populations, which are qualitatively and quantitatively worse in ND patients.

These observations highlight the need to develop novel therapeutic agents that are specifically designed to not only demonstrate efficacy against these particular disabling symptoms but to also possess tolerability in these specific patient populations. This can be achieved by improving the selectivity of the drug target interactions of new therapeutic agents. Specifically, the development of agents with novel mechanisms of action that avoid the known pitfalls associated with existing agents is desired. In addition, improved selectivity can avoid the known adverse effects associated with interactions with non-efficacy conferring drug targets.

BRIEF DESCRIPTION OF THE DRAWINGS

FIG. 1 shows plots of $D_2$ and 5-HT2A receptor agonist activity of Parkinson's Disease therapeutics as determined by the physiologically predictive, cell-based, in vivo R-SAT assay.

SUMMARY OF THE INVENTION

Figure 1A:
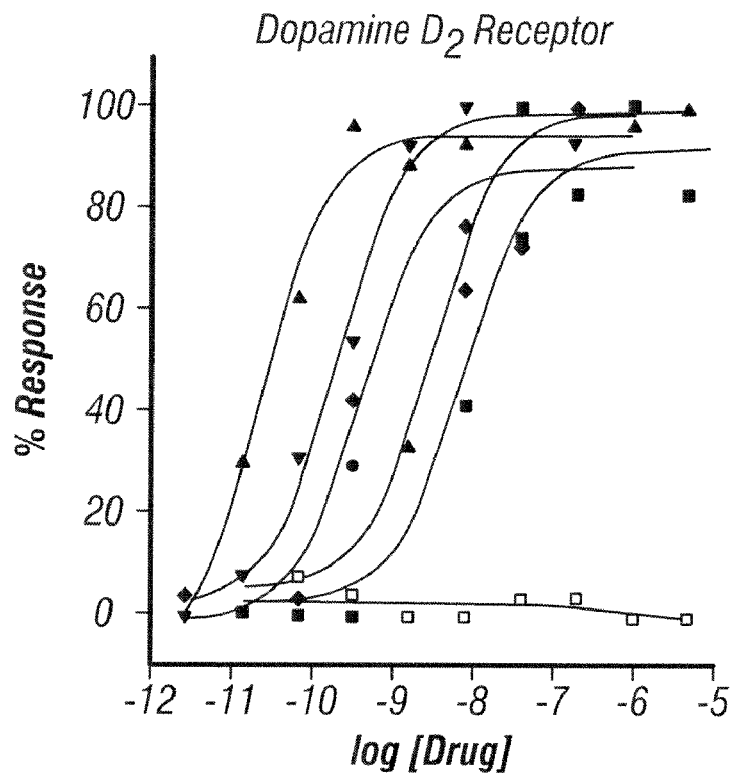
FIG. 1A plots drug activity at human $D_2$ receptors.

Disclosed herein is a composition comprising a compound of Formula (I):

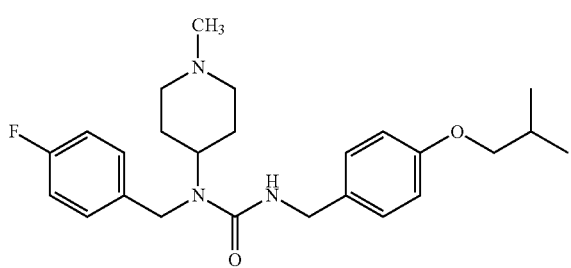

(I)

and a pharmaceutically acceptable carrier. In some embodiments, the composition further comprises an additional therapeutic agent. In some embodiments the additional therapeutic agent is selected from levodopa (SINEMET™, SINEMET-CR™, bromocriptine (PARLODEL™), pergolide (PERMAX™), ephedrine sulfate (EPHEDRINE™), pemoline CYLERT™), mazindol (SANOREX™), d,l-α-methylphenethylamine (ADDERALL™), methylphenydate (RITALIN™), pramipexole (MIRAPEX™), modafinil (PROVIGIL™), and ropinirole (REQUIP™). In other embodiments, the additional therapeutic agent is an anti-dyskensia agent selected from baclofen (Lioresal™), botulinum toxin (Botox™), clonazepam (Klonopin™), and diazepam (Valium™). In other embodiments, the additional therapeutic agent is an anti-dystonia, anti-myoclonus, or anti-tremor agent selected from baclofen (LIORESAL™), botulinum toxin (BOTOX™), clonazepam (KLONOPIN™), and diazepam (VALIUM™). In other embodiments, the additional therapeutic agent is an anti-psychotic agent with dopaminergic receptor antagonism. In some embodiments, the additional therapeutic agent is an anti-psychotic agent selected from chlorpromazine (THORAZINE™), haloperodol (HALDOL™), molindone (MOBAN™), thioridazine (MELLARIL™), a phenothiazine, a butyrophenome, diphenulbutylpiperinde (pimozide), thioxanthines (fluphenthixol), substituted benzamides (sulpiride), sertindole, amisulpride, risperidone, clozapine, olanzapine, ziprasidone, aripiprazole, and their active metabolites (N-desmethylclozapine, N-desmethylolanzapine, 9-OH-risperdone)).

Also disclosed herein is a method for treating a neurodegenerative disease comprising: identifying a patient suffering from a neurodegenerative disease and administering to the patient an effective amount of an inverse agonist selective for a serotonin receptor; whereby the dopaminergic therapy associated dyskinesia is reduced. In some embodiments, the neurodegenerative disease is Parkinson's disease, Huntington's disease, Alzheimer's disease, Spinocerebellar Atrophy, Tourette's Syndrome, Friedrich's Ataxia, Machado-Joseph's disease, Lewy Body Dementia, Dystonia, Progressive Supranuclear Palsy, or Frontotemporal Dementia. In one embodiment, the serotonin receptor is a 5HT2A receptor. In another embodiment, the serotonin receptor is a 5HT2C receptor. In some embodiments, the inverse agonist binds to a 5HT2A receptor or a 5HT2C receptor. In some embodiments, the inverse agonist is the compound of formula (I). One embodiment further comprises administering a dopaminergic agent in combination with the compound of formula (I). In some embodiments, the reagent increases dopaminergic activity and is selected from the group consisting of levodopa, SINAMET™, SINAMETCR™, bromocriptine (PARLODEL™), pergolide (PERMAX™), ephedrine sulfate (EPHEDRINE™), pemoline CYLERT™), mazindol (SANOREX™), d,l-α-methylphenethylamine (ADDERALL™), methylphenydate (RITALIN™), pramipexole (MIRAPEXT™), modafinil (PROVIGIL™), and ropinirole (REQUIP™).

Also disclosed herein is, a method for treating dyskinesia associated with dopaminergic therapy comprising: identifying a patient suffering from dopaminergic therapy associated dyskinesia and administering to the patient an effective amount of an inverse agonist selective for a serotonin receptor; whereby the dopaminergic therapy associated dyskinesia is reduced. In one embodiment the serotonin receptor is a 5HT2A receptor. In another embodiment the serotonin receptor is a 5HT2C receptor. In some embodiments, the inverse agonist binds to a 5HT2A receptor and a 5HT2C receptor. In one embodiment, the inverse agonist is the compound of formula (I). Some embodiments further comprise administering an anti-dyskensia agent in combination with the compound of formula (I). In some embodiments, the anti-dyskinesia agent is selected from the group consisting of baclofen (Lioresal™), botulinum toxin (Botox™), clonazepam (Klonopin™), and diazepam (Valium™). In some embodiments, the patient suffers from a neurodegenerative disease selected from the group consisting of Parkinson's disease, Huntington's disease, Alzheimer's disease, Spinocerebellar Atrophy, Tourette's Syndrome, Friedrich's Ataxia, Machado-Joseph's disease, Lewy Body Dementia, Dystonia, Progressive Supranuclear Palsy, and Frontotemporal Dementia.

Further disclosed herein is a method for treating dystonia, myoclonus, or tremor associated with dopaminergic therapy comprising: identifying a patient suffering from dopaminergic therapy associated dystonia, myoclonus, or tremor; and administering to the patient an effective amount of an inverse agonist selective for a serotonin receptor; whereby the dopaminergic therapy associated dystonia, myoclonus, or tremor is reduced. In one embodiment the serotonin receptor is a 5HT2A receptor. In another embodiment, the serotonin receptor is a 5HT2C receptor. In some embodiments, the inverse agonist binds to a 5HT2A receptor and a 5HT2C receptor. In some embodiments, the inverse agonist is the compound of formula (I). Some embodiments further comprise an anti-dystonia, anti-myoclonus, or anti-tremor agent in combination with the compound of formula (I). In some embodiments, the anti-dystonia, anti-myoclonus, or anti-tremor agent is selected from the group consisting of baclofen (LIORESAL™), botulinum toxin (BOTOX™), clonazepam (KLONOPIN™), and diazepam (VALIUM™).

Also disclosed herein is a method for treating psychosis associated with dopaminergic therapy comprising: identifying a patient suffering from dopaminergic therapy associated psychosis; and administering to the patient an effective amount of an inverse agonist selective for a serotonin receptor; whereby symptoms of dopaminergic therapy associated psychosis is reduced. In one embodiment the serotonin receptor is a 5HT2A receptor. In another embodiment the serotonin receptor is a 5HT2C receptor. In some embodiments the inverse agonist binds to a 5HT2A receptor and a 5HT2C receptor. In some embodiments the inverse agonist is the compound of formula (I). Some embodiments further comprise an anti-psychotic agent in combination with the compound of formula (I). In some embodiments, the anti-psychotic agent is selected from the group consisting of chlorpromazine (THORAZINE™), haloperodol (HALDOL™), molindone (MOBAN™), thioridazine (MELLARIL™), a phenothiazine, a butyrophenome, diphenulbutylpiperinde (pimozide), thioxanthines (fluphenthixol), substituted benzamides (sulpiride), sertindole, amisulpride, risperidone, clozapine, olanzapine, ziprasidone, aripiprazole, and their active metabolites (N-desmethylclozapine, N-desmethylolanzapine, 9-OH-risperdone)). In some embodiments, the patient suffers from a neurodegenerative disease selected from the group consisting of Parkinson's disease, Huntington's disease, Alzheimer's disease, Spinocerebellar Atrophy, Tourette's Syndrome, Friedrich's Ataxia, Machado-Joseph's disease, Lewy Body Dementia, Dystonia, Progressive Supranuclear Palsy, and Frontotemporal Dementia.

Also disclosed herein is a method for treating a neuropsychiatric disease comprising: identifying a patient suffering from a neuropsychiatric disease; and administering to the patient an effective amount of an inverse agonist selective for a serotonin receptor. In some embodiments, the neuropsychiatric disease is selected from the group consisting of schizophrenia, schizoaffective disorders, mania, behavioral disturbances associated with dementia and psychotic depression. In some embodiments the serotonin receptor is a 5HT2A receptor. In some embodiments the serotonin receptor is a 5HT2C receptor. In some embodiments the inverse agonist binds to a 5HT2A receptor or a 5HT2C receptor. In one embodiment, the inverse agonist is the compound of formula (I). Some embodiments further comprise administering an antipsychotic agent in combination with the inverse agonist, the anti-psychotic agent selected from the group consisting of chlorpromazine (THORAZINE™), haloperodol (HALDOL™), molindone (MOBAN™), thioridazine (MELLARIL™), a phenothiazine, a butyrophenome, diphenulbutylpiperinde (pimozide), thioxanthines (fluphenthixol), substituted benzamides (sulpiride), sertindole, amisulpride, risperidone, clozapine, olanzapine, ziprasidone, aripiprazole, and their active metabolites (N-desmethylclozapine, N-desmethylolanzapine, 9-OH-risperdone)).

Also disclosed herein is a compound having the structure of Formula (I):

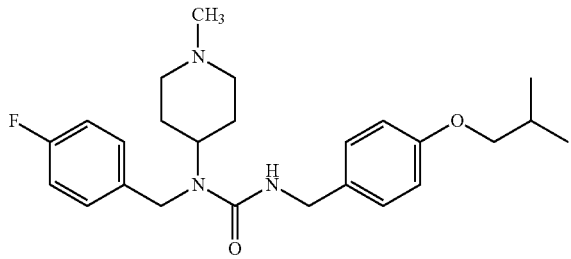

(I)

Additionally disclosed herein is a method of inhibiting an activity of a monoamine receptor comprising contacting the monoamine receptor or a system containing the monoamine receptor with an amount of the compound of formula (I) that is effective in inhibiting the activity of the monoamine receptor. In some embodiments, the monoamine receptor is a serotonin receptor. In one embodiment the serotonin receptor is the 5-HT2A subclass. In some embodiments the serotonin receptor is in the central nervous system. In some embodiments the serotonin receptor is in the peripheral nervous system. In some embodiments the serotonin receptor is in blood cells or platelets. In some embodiments the serotonin receptor is mutated or modified. In some embodiments the activity is signaling activity. In some embodiments the activity is constitutive. In some embodiments the activity is associated with serotonin receptor activation.

Also disclosed herein is a method of inhibiting an activation of a monoamine receptor comprising contacting the monoamine receptor or a system containing the monoamine receptor with an amount of the compound of formula (I) that is effective in inhibiting the activation of the monoamine receptor. In some embodiments, the activation is by an agonistic agent. In some embodiments the agonistic agent is exogenous. In some embodiments the agonistic agent is endogenous. In some embodiments the activation is constitutive. In some embodiments the monoamine receptor is a serotonin receptor. In some embodiments the serotonin receptor is the 5-HT2A subclass. In some embodiments the serotonin receptor is in the central nervous system. In some embodiments the serotonin receptor is in the peripheral nervous system. In some embodiments the serotonin receptor is in blood cells or platelets. In some embodiments the serotonin receptor is mutated or modified.

Also disclosed herein is a method of treating a disease condition associated with a monoamine receptor comprising administering to a subject in need of such treatment a therapeutically effective amount of the compound of formula (I). In some embodiments the disease condition is selected from the group consisting of schizophrenia, psychosis, migraine, hypertension, thrombosis, vasospasm, ischemia, depression, anxiety, sleep disorders and appetite disorders. In some embodiments the disease condition is associated with dysfunction of a monoamine receptor. In some embodiments, the disease condition is associated with activation of a monoamine receptor. In some embodiments, the disease condition is associated with increased activity of monoamine receptor. In some embodiments, the monoamine receptor is a serotonin receptor. In some embodiments the serotonin receptor is the 5-HT2A subclass. In some embodiments the serotonin receptor is in the central nervous system. In some embodiments the serotonin receptor is in the peripheral nervous system. In some embodiments the serotonin receptor is in blood cells or platelets. In some embodiments, the serotonin receptor is mutated or modified.

Also disclosed herein is a method of treating schizophrenia comprising administering to a subject in need of such treatment a therapeutically effective amount the compound of formula (I).

Also disclosed herein is a method of treating migraine comprising administering to a subject in need of such treatment a therapeutically effective amount of the compound of formula (I).

Also disclosed herein is a method of treating psychosis comprising administering to a subject in need of such treatment a therapeutically effective amount of the compound of formula (I).

Also disclosed herein is a method for identifying a genetic polymorphism predisposing a subject to being responsive the compound of formula (I), comprising: administering to a subject a therapeutically effective amount of said compound; measuring the response of said subject to said compound, thereby identifying a responsive subject having an ameliorated disease condition associated with a monoamine receptor; and identifying a genetic polymorphism in the responsive subject, wherein the genetic polymorphism predisposes a subject to being responsive to said compound. In some embodiments the ameliorated disease condition is associated with the 5-HT class or 5-HT2A subclass of monoaminergic receptors.

Additionally disclosed herein is a method for identifying a subject suitable for treatment with the compound of Formula (I), comprising detecting the presence of a polymorphism in a subject wherein the polymorphism predisposes the subject to being responsive to the compound, and wherein the presence of the polymorphism indicates that the subject is suitable for treatment with the compound of formula (I).

DETAILED DESCRIPTION OF THE PREFERRED EMBODIMENTS

Definitions

For the purpose of the current disclosure, the following definitions shall in their entireties be used to define technical terms, and shall also, in their entireties, be used to define the scope of the composition of matter for which protection is sought in the claims.

"Constitutive activity" is defined as the elevated basal activity of a receptor that is independent of the presence of an agonist. Constitutive activity of a receptor may be measured using a number of different methods, including cellular (e.g., membrane) preparations (see, e.g., Barr &. Manning, *J. Biol. Chem.* 272:32979-87 (1997)), purified reconstituted receptors with, or without the associated G-protein in phospholipid vesicles (Cerione et al., *Biochemistry* 23:4519-25 (1984)), and functional cellular assays (U.S. Patent Application Ser. No. 60/103,317) or any other method known in the art.

"Agonist" is defined as a compound that increases the basal activity of a receptor when it contacts the receptor.

An "antagonist" is defined as a compound that competes with an agonist or inverse agonist for binding to a receptor, thereby blocking the action of an agonist or inverse agonist on the receptor. However, an antagonist (also known as a "neutral" antagonist) has no effect on constitutive receptor activity.

An "inverse agonist" is defined as a compound that decreases the basal activity of a receptor (i.e., signaling mediated by the receptor). Such compounds are also known as negative antagonists. An inverse agonist is a ligand for a receptor that causes the receptor to adopt an inactive state relative to a basal state occurring in the absence of any ligand. Thus, while an antagonist can inhibit the activity of an agonist, an inverse agonist is a ligand that can alter the conformation of the receptor in the absence of an agonist. The concept of an inverse agonist has been explored by Bond et al. in *Nature* 374:272 (1995). More specifically, Bond et al. have proposed that unliganded $\beta_2$-adrenoceptor exists in an equilibrium between an inactive conformation and a spontaneously active conformation. Agonists are proposed to stabilize the receptor in an active conformation. Conversely, inverse agonists are believed to stabilize an inactive receptor conformation. Thus, while an antagonist manifests its activity by virtue of inhibiting an agonist, an inverse agonist can additionally manifest its activity in the absence of an agonist by inhibiting the spontaneous conversion of an unliganded receptor to an active conformation.

The "5-HT2A receptor" is defined as a receptor, having an activity corresponding to the activity of the human serotonin receptor subtype, which was characterized through molecular cloning and pharmacology as detailed in Saltzman et al., *Biochem. Biophys. Res. Comm.* 181:1469-78; and Julius et al., *Proc. Natl. Acad. Sci. USA* 87:928-932, the disclosures of which are incorporated herein by reference in their entireties.

The term "subject" refers to an animal, preferably a mammal, most preferably a human, who is the object of treatment, observation or experiment.

"Selective" is defined as a property of a compound whereby an amount of the compound sufficient to effect a desired response from a particular receptor type, subtype, class or subclass with significantly less or substantially little or no effect upon the activity other receptor types. For example, a selective compound may have at least a 10-fold greater effect on activity of the desired receptor than on other receptor types. In some cases, a selective compound may have at least a 20-fold greater effect on activity of the desired receptor than on other receptor types, or at least a 50-fold greater effect, or at least a 100-fold greater effect, or at least a 1000-fold greater effect, or at least a 10,000-fold greater effect, or at least a 100,000-fold greater effect, or more than a 100,000-fold greater effect. "Selectivity" or "selective," as an inverse agonist is understood as a property of the compound of the invention whereby an amount of compound that effectively inversely agonizes the 5-HT2A receptor, and thereby decreases its activity, causes little or no inverse agonistic or antagonistic activity at other, related or unrelated, receptors. In particular, in one embodiment, a compound has surprisingly been found not to interact strongly with other serotonin receptors (5-HT 1A, 1B, 1D, 1E, 1F, 2B, 2C, 4A, 6, and 7) at concentrations where the signaling of the 5-HT2A receptor is strongly or completely inhibited. In one embodiment, the compound is also selective with respect to other monoamine-binding receptors, such as the dopaminergic, histaminergic, adrenergic and muscarinic receptors. Compounds that are highly selective for 5-HT2A receptors may have a beneficial effect in the treatment of psychosis, schizophrenia or similar neuropsychiatric disorders, while avoiding adverse effects associated with drugs hitherto suggested for this purpose.

Some embodiments described herein relate to serotonin 2A or 2C receptor inverse agonists, including compositions and methods for treating certain side-effects caused or exacerbated by dopaminergic agent-associated therapies commonly used in treating neurodegenerative diseases. For example, the compounds disclosed herein have utility in reducing dyskinesia and psychosis associated with dopaminergic therapies used in treating Parkinson's disease, a neurodegenerative disease. According to one embodiment, the compound N-(1-methylpiperidin-4-yl)-N-(4-fluorophenyl-methyl)-N'-(4-(2-methylpropyloxy)phenylmethyl)carbamide having the structure of formula (I) is provided:

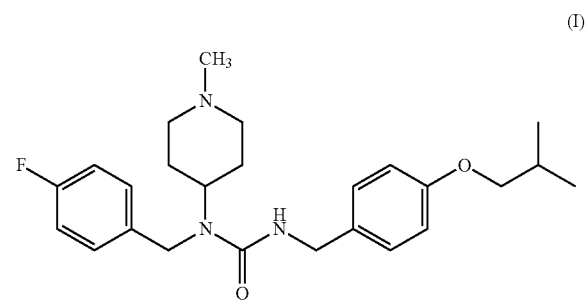

(I)

One embodiment relates to a composition comprising the compound of formula (I) and a pharmaceutically acceptable carrier. The composition may also contain other compounds such as compounds for treating dyskensia, dystonia, or psychosis.

According to one embodiment, the tartrate salt of the compound, N-(1-methylpiperidin-4-yl)-N-(4-fluorophenylmethyl)-N'-(4-(2-methylpropyloxy)phenylmethyl)carbamide is a potent, selective, orally bioavailable 5-HT2A receptor inverse agonist. The compound of formula (I) also possesses lesser potency as a 5-HT2C receptor inverse agonist and lacks intrinsic activity at the remaining monoaminergic receptor subtypes. Perhaps most notably, the compound of formula (I) lacks activity at dopamine receptor subtypes. (See U.S. patent application Ser. No. 09/800,096, which is hereby incorporated by reference in its entirety). Extensive behavioral pharmacological profiling of the compound of formula (I), including pre-clinical models of antipsychotic and anti-dyskinetic drug actions, support the therapeutic use of the compound in Parkinson's Disease and related human neurodegenerative diseases.

Parkinson's Disease (PD) is a common and progressive neurodegenerative disease. Current estimates suggest that nearly 900,000 individuals in the United States have PD and that the prevalence is increasing as the US population ages. Dopamine receptor agonists are used to alleviate the symptoms of PD, such as motoric dysfunction. Unfortunately, the protracted use of these dopaminergic agents causes, over time, neuropsychiatric (psychosis) and troublesome motor (dyskinesia) side effects in 30 to 80% of patients, respectively.

Antipsychotics and dopamine receptor antagonists can be effective in ameliorating these adverse effects. Unfortunately, many of these compounds significantly worsen motor function in PD patients secondary to their hypo-dopaminergic state. Biochemical and pharmacological data support the hypothesis that potentiation of serotonergic neurotransmission may be pathophysiologically related to the development of dyskinesias and psychosis in these patients. While not being bound by this theory, the compounds disclosed herein were selected to exploit the relationship of serotonergic activity and the negative side-effects associated with dopaminergic therapy.

L-dopa is a typical dopaminergic compound used to treat PD. L-dopa has been shown to increase central serotonin release, turnover, and metabolite concentrations in rodent brain. Direct acting dopamine receptor agonists like pergolide possess, in additional to their dopamine receptor agonist properties, potent agonist activity at serotonin 2A (5-HT2A) and 2C (5-HT2C) receptors as demonstrated by various in vitro pharmacological assays.

In one embodiment, the compounds disclosed herein can be used to treat many side-effects that arise from dopaminergic therapy. For example, the disclosed compounds are also useful for treatment of dyskinesia or psychosis caused or exacerbated as a side-effect of other therapeutic agents such as L-dopa. In one embodiment, the compounds are preferably used for the treatment of dyskinesia or psychosis associated with L-dopa treatment.

The compounds may be used to treat existing dyskinesia or psychosis or may be used prophylactic fashion when for example, it is considered necessary to initiate L-dopa therapy and it is feared that dyskinesia or psychosis may develop.

The compounds may be used to treat dyskinesia or psychosis as a monotherapy or as an adjunct to medicaments to prevent or treat dyskinesia or psychosis side-effects caused by the medicament or alternatively the compounds may be given in combination with other compounds which also reduce dyskinesia.

In some embodiments, the compounds described herein can be formulated into compositions for administration to patients in need thereof. Appropriate compositions can take a number of different forms depending on how the composition is to be used. For example, the composition may be in the form of a powder, tablet, capsule, liquid, ointment, cream, gel, hydrogel, aerosol spray, micelle, liposome or any other pharmaceutically acceptable form. One of ordinary skill in the art would readily appreciate that an appropriate vehicle for use with the disclosed compounds of the invention should be one that is well tolerated by a recipient of the composition. The vehicle should also readily enable the delivery of the compounds to appropriate target receptors. For example, one of ordinary skill in the art would know to consult *Pharmaceutical Dosage Forms and Drug Delivery Systems*, by Ansel, et al., Lippincott Williams & Wilkins Publishers; 7th ed. (1999) or a similar text for guidance regarding such formulations.

The composition of the invention may be used in a number of ways. For instance, systemic administration may be required in which case the disclosed compounds can be formulated into a composition that can be ingested orally in the form of a tablet, capsule or liquid. Alternatively the composition may be administered by injection into the blood stream. Injections may be intravenous (bolus or infusion) or subcutaneous (bolus or infusion). The disclosed compounds can also be administered centrally by means of intracerebral, intracerebroventricular, or intrathecal delivery.

The compound may also be used with a time delayed release device. Such devices may, for example, be inserted under the skin and the compound may be released over weeks or months. Such a device may be particularly useful for patients with long term dyskinesia such as patients on continuous L-dopa therapy for the treatment of PD. The devices may be particularly advantageous when a compound is used which would normally require frequent administration (e.g., frequent injection).

It will be readily appreciated that the amount of a compound required is determined by biological activity and bioavailability which in turn depends on the mode of administration, the physicochemical properties of the compound employed and whether the compound is being used as a monotherapy or in a combined therapy. The frequency of administration will also be influenced by the above mentioned factors and particularly the half-life of the compound within the subject being treated.

One of ordinary skill in the art would appreciate that specific formulations of compositions and precise therapeutic regimes (such as daily doses of the compounds and the frequency of administration) can be determined using known procedures. Such procedures conventionally employed by the pharmaceutical industry include in vivo experimentation and clinical trials.

Generally, a daily dose of between 0.01 µg/kg of body weight and 1.0 g/kg of body weight of a serotonin 2A/2C receptor inverse agonist can be used with the methods disclosed herein. In one embodiment, the daily dose is between 0.01 mg/kg of body weight and 100 mg/kg of body weight, or any milligram or half-milligram quantity in this disclosed range, e.g., 1.5, 2, 2.5, etc.

Daily doses may be given as a single administration (e.g. a daily tablet for oral consumption or as a single daily injection). Alternatively the compound used may require administration twice or more times during a day, depending on the kinetics of the drug associated with the individual patient. Alternatively a slow release device may be used to provide optimal doses to a patient without the need to administer repeated doses.

Biochemical Evidence

The cornerstone of current pharmacological intervention in PD remains L-dopa based therapies. L-dopa readily crosses the blood brain barrier, is taken up by neurons and undergoes rapid enzymatic conversion to dopamine, via L-aromatic acid decarboxylase (LAAD) activity in dopaminergic neurons. The increased availability and release of dopamine from these neurons clearly leads to increased dopaminergic transmission, and clinical efficacy in reversing the motoric effects of the hypo-dopaminergic state observed in PD. However, L-dopa lacks specificity for dopaminergic systems, and LAAD is widely expressed in brain. Early biochemical observations in rat brain noted that L-dopa substantially reduced central serotonergic stores, and increased the concentration of the principle serotonin metabolite of 5-hydroxyindoleacetic acid (5-HIAA) (1). Histochemical approaches have demonstrated that L-dopa accumulates in serotonergic neurons, and neurotransmitter release experiments have demonstrated that L-dopa markedly increased the release of both dopamine and serotonin, that release of serotonin is dependent upon LARD activity, and that it is not eliminated by the selective destruction of dopaminergic neurons (2,3). These observations suggest that the administration of L-dopa to PD patients results in marked increases in the release of central serotonin, potentiating serotonergic neurotransmission. Finally, post-mortem biochemical analysis of PD patients that developed psychosis, when compared to a matched group that did not develop neuropsychiatric disturbances, found that the patients with psychosis had significant elevations in serotonin and 5-HIAA levels in multiple cortical and sub-cortical structures, most notably various mesencephalic nuclei including the red nucleus (4).

Serotonin or 5-hydroxytryptamine (5-HT) plays a significant role in the functioning of the mammalian body. In the central nervous system, 5-HT is an important neurotransmitter and neuromodulator that is implicated in such diverse behaviors and responses as sleeping, eating, locomotion, perceiving pain, learning and memory, sexual behavior, controlling body temperature and blood pressure. In the spinal column, serotonin plays an important role in the control systems of the afferent peripheral nociceptors (Moulignier, *Rev. Neural.* 150:3-15, (1994)). Peripheral functions in the cardiovascular, hematological, and gastrointestinal systems have also been ascribed to 5-HT. 5-HT has been found to mediate a variety of contractile, secretory, and electrophysiologic effects including vascular and nonvascular smooth muscle contraction, and platelet aggregation. (Fuller, *Biology of Serotonergic Transmission,* 1982; Botillin, *Serotonin In Mental Abnormalities* 1:316 (1978); Barchas, et al., *Serotonin and Behavior,* (1973)). The 5-HT2A receptor subtype (also referred to as subclass) is widely yet discretely expressed in the human brain, including many cortical, limbic, and forebrain regions postulated to be involved in the modulation of higher cognitive and affective functions. This receptor subtype is also expressed on mature platelets where it mediates, in part, platelet aggregation, one of the initial steps in the process of vascular thrombosis.

Given the broad distribution of serotonin within the body, it is understandable that tremendous interest in drugs that affect serotonergic systems exists (Gershon, et al, *The Peripheral Actions of 5-Hydroxytryptamine,* 246 (1989); Saxena, et al, *J. Cardiovascular Pharmacol.* 15: Supp. 7 (1990)). Serotonin receptors are members of a large human gene family of membrane-spanning proteins that function as transducers of intercellular communication. They exist on the surface of various cell types, including neurons and platelets, where, upon their activation by either their endogenous ligand serotonin or exogenously administered drugs, they change their conformational structure and subsequently interact with downstream mediators of cellular signaling. Many of these receptors, including the 5-HT2A subclass, are G-protein coupled receptors (GPCRs) that signal by activating guanine nucleotide binding proteins (G-proteins), resulting in the generation, or inhibition of, second messenger molecules such as cyclic AMP, inositol phosphates, and diacylglycerol. These second messengers then modulate the function of a variety of intracellular enzymes, including kinases and ion channels, which ultimately affect cellular excitability and function.

At least 15 genetically distinct 5-HT receptor subtypes have been identified and assigned to one of seven families (5-HT1-7). Each subtype displays a unique distribution, preference for various ligands, and functional correlate(s). Serotonin may be an important component in various types of pathological conditions such as certain psychiatric disorders (depression, aggressiveness, panic attacks, obsessive compulsive disorders, psychosis, schizophrenia, suicidal tendency), certain neurodegenerative disorders (Alzheimer-type dementia, Parkinsonism, Huntington's chorea), anorexia, bulimia, disorders associated with alcoholism, cerebral vascular accidents, and migraine (Meltzer, *Neuropsychopharmacology,* 21:106 S-115S (1999); Barnes & Sharp, *Neuropharmacology,* 38:1083-1152 (1999); Glennon, *Neurosci. Biobehavioral Rev.,* 14:35 (1990)). Recent evidence strongly implicates the 5-HT2 receptor subtype in the etiology of such medical conditions as hypertension, thrombosis, migraine, vasospasm, ischemia, depression, anxiety, psychosis, schizophrenia, sleep disorders and appetite disorders.

Schizophrenia is a particularly devastating neuropsychiatric disorder that affects approximately 1% of the human population. It has been estimated that the total financial cost for the diagnosis, treatment, and lost societal productivity of individuals affected by this disease exceeds 2% of the gross national product (GNP) of the United States. Current treatment primarily involves pharmacotherapy with a class of drugs known as antipsychotics. Antipsychotics are effective in ameliorating positive symptoms (e.g., hallucinations and delusions), yet they frequently do not improve negative symptoms (e.g., social and emotional withdrawal, apathy, and poverty of speech).

Currently, nine major classes of antipsychotics are prescribed to treat psychotic symptoms. Use of these compounds is limited, however, by their side effect profiles. Nearly all of the "typical" or older generation compounds have significant adverse effects on human motor function. These "extrapyramidal" side effects, so termed due to their effects on modulatory human motor systems, can be both acute (e.g., dystonic reactions, a potentially life threatening but rare neuroleptic malignant syndrome) and chronic (e.g., akathisias, tremors, and tardive dyskinesia). Drug development efforts have, therefore, focused on newer "atypical" agents free of these adverse effects.

Antipsychotic drugs have been shown to interact with a large number of central monoaminergic neurotransmitter receptors, including dopaminergic, serotonergic, adrenergic, muscarinic, and histaminergic receptors. It is likely that the therapeutic and adverse effects of these drugs are mediated by distinct receptor subtypes. The high degree of genetic and pharmacological homology between these receptor subtypes has hampered the development of subtype-selective compounds, as well as the determination of the normal physiologic or pathophysiologic role of any particular receptor subtype. Thus there is a need to develop drugs that are selective for individual receptor classes and subclasses amongst monoaminergic neurotransmitter receptors.

The prevailing theory for the mechanism of action of antipsychotic drugs involves antagonism of dopamine D2 receptors. Unfortunately, it is likely that antagonism of dopamine D2 receptors also mediates the extrapyramidal side effects. Antagonism of 5-HT2A is an alternate molecular mechanism for drugs with antipsychotic efficacy, possibly through antagonism of heightened or exaggerated signal transduction through serotonergic systems. 5-HT2A antagonists are therefore good candidates for treating psychosis without extrapyramidal side effects.

Traditionally, these receptors have been assumed to exist in a quiescent state unless activated by the binding of an agonist (a drug that activates a receptor). It is now appreciated that many, if not most, of the GPCR monoamine receptors, including serotonin receptors, can exist in a partially activated state in the absence of their endogenous agonists. This increased basal activity (constitutive activity) can be inhibited by compounds called inverse agonists. Both agonists and inverse agonists possess intrinsic activity at a receptor, in that they alone can activate or inactivate these molecules, respectively. In contrast, classic or neutral antagonists compete against agonists and inverse agonists for access to the receptor, but do not possess the intrinsic ability to inhibit elevated basal or constitutive receptor-responses.

We have elucidated an important aspect of 5-HT2A receptor function by applying the Receptor Selection and Amplification Technology (U.S. Pat. No. 5,707,798, 1998; Chem. Abstr. 128:111548 (1998) and citations therein), to the study of the 5-HT2 subclass of serotonin receptors. R-SAT is a phenotypic assay of receptor function that involves the heterologous expression of receptors in mammalian fibroblasts. Using this technology we were able to demonstrate that native 5-HT2A receptors possess significant constitutive, or agonist-independent, receptor activity (U.S. Patent Application Ser. No. 60/103,317, herein incorporated by reference). Furthermore, by directly testing a large number of centrally acting medicinal compounds with known clinical activity in neuropsychiatric disease, we determined that compounds with antipsychotic efficacy all shared a common molecular property. Nearly all of these compounds, which are used by psychiatrists to treat psychosis, were found to be potent 5-HT2A inverse agonists. This unique clinico-pharmacologic correlation at a single receptor subtype is compelling evidence that 5-HT2A receptor inverse agonism is a molecular mechanism of antipsychotic efficacy in humans.

Detailed pharmacological characterization of a large number of antipsychotic compounds revealed that they possess broad activity at multiple related receptor subtypes. Most of these compounds display agonist, competitive antagonist, or inverse agonist activity at multiple monoaminergic receptor subtypes, including serotoninergic, dopaminergic, adrenergic, muscarinic and histaminergic receptors. This broad activity is likely responsible for the sedating, hypotensive, and motor side effects of these compounds. It would therefore be of great advantage to develop compounds that are selective inverse agonists of the 5-HT2A receptor, but which have little or no activity on other monamine receptor subtypes, especially dopamine D2 receptors. Such compounds may be useful in the treatment of human disease (e.g., as anti-psychotics), and may avoid the adverse side effects associated with non-selective receptor interactions.

The compound of formula (I) is active at monoamine receptors, specifically serotonin receptors. In one embodiment, the compound acts as inverse agonist at the 5-HT2A receptor. Thus, experiments performed on cells transiently expressing the human phenotype of said receptor have shown that the compound of formula (I) attenuates the signaling of such receptors in the absence of additional ligands acting upon the receptor. The compound has thus been found to possess intrinsic activity at this receptor and is able to attenuate the basal, non-agonist-stimulated, constitutive signaling responses that the 5-HT2A receptor displays. The observation that the compound of formula (I) is an inverse agonist also indicates that the compound has the ability to antagonize the activation of 5-HT2A receptors that is mediated by endogenous agonists or exogenous synthetic agonist ligands.

In one embodiment, the compound of formula (I) shows a relatively high degree of selectivity towards the 5-HT2A subtype of serotonin receptors relative to other subtypes of the serotonin (5-HT) family of receptors as well as to other receptors, most particularly the monoaminergic G-protein coupled receptors, such as dopamine receptors.

The compound of formula (I) may therefore be useful for treating or alleviating symptoms of disease conditions associated with impaired function, in particular elevated levels of activity, of especially 5-HT2A receptors, whether this impaired function is associated with improper levels of receptor stimulation or phenotypical aberrations.

Others have previously hypothesized that certain neuropyschological diseases might be caused by altered levels of constitutive activity of monoamine receptors. Such constitutive activity might be modified via contacting the relevant receptor with a synthetic inverse agonist. By directly testing a large number of centrally acting medicinal compounds with known clinical activity in neuropsychiatric disease, we determined that compounds with antipsychotic efficacy all shared a common molecular property. Nearly all of these compounds that are used by psychiatrists to treat psychosis were found to be potent 5-HT2A inverse agonists. This correlation is compelling evidence that 5-HT2A receptor inverse agonism is a molecular mechanism of antipsychotic efficacy in humans.

Detailed pharmacological characterization of a large number of antipsychotic compounds in our laboratory revealed that they possess broad activity at multiple related receptor subtypes. Most of these compounds display either agonist, competitive antagonist, or inverse agonist activity at multiple monoaminergic receptor subtypes including serotoninergic, dopaminergic, adrenergic, muscarinic and histaminergic receptors. This broad activity is likely responsible for the sedating, hypotensive, and motor side effects of these compounds. In one embodiment, the compound of formula (I) possesses efficacy as, for example, a novel antipsychotic, but will have fewer or less severe side effects than existing compounds.

In one embodiment a method is provided to inhibit activity of a monoamine receptor. This method comprises contacting a monoamine receptor or a system containing the monamine receptor, with an effective amount of the compound of formula (I). According to one embodiment, the monamine receptor is a serotonin receptor. In one embodiment, the compound is selective for the 5-HT2A receptor subclass. In another embodiment, the compound has little or substantially no activity to other types of receptors, including other serotonergic receptors and most particularly, monoaminergic G-protein coupled receptors, such as dopaminergic receptors.

The system containing the monoamine receptor may, for example, be a subject such as a mammal, non-human primate or a human. The receptor may be located in the central or peripheral nervous system, blood cells or platelets.

The system may also be an in viva or in vitro experimental model, such as a cell culture model system that expresses a monamine receptor, a cell-free extract thereof that contains a monoamine receptor, or a purified receptor. Non-limiting examples of such systems are tissue culture cells expressing the receptor or extracts or lysates thereof. Cells that may be used in the present method include any cells capable of mediating signal transduction via monoamine receptors, especially the 5-HT2A receptor, either via endogenous expression of this receptor (e.g., certain types of neuronal cells lines, for example, natively express the 5-HT2A receptor), or following transfection of cells with plasmids containing the receptor gene. Such cells are typically mammalian cells (or other eukaryotic cells, such as insect cells or *Xenopus* oocytes), because cells of lower organisms generally lack the appropriate signal transduction pathways for the present purpose. Examples of suitable cells include: the mouse fibroblast cell line NIH 3T3 (ATCC CRL 1658), which responds to transfected 5-HT2A receptors by stimulating growth; RAT 1 cells (Pace et al., *Proc. Natl. Acad. Sci. USA* 88:7031-35 (1991)); and pituitary cells (Vallar et al., *Nature* 330:556-58 (1987). Other useful mammalian cells for the present method include HEK 293 cells, CHO cells, and COS cells.

One embodiment provides methods of inhibiting activity of a native, mutated or modified monoamine receptor. Also provided are kits for performing the same. In one embodiment, the activity of the receptor is a signaling activity. In another embodiment, the activity of the receptor is the constitutive basal activity of the receptor.

In one embodiment, the activity of the receptor is a response, such as a signaling response, to an endogenous agonist, such as 5-HT, or an exogenous agonistic agent, such as a drug or other synthetic ligand. The compound of formula (I) may act by either inversely agonizing or antagonizing the receptor.

In one embodiment, the compound of formula (I) is an inverse agonist selective for the 5-HT2A receptor and the compound has little or substantially no activity toward other serotonergic or other monoaminergic receptors, such as dopaminergic receptors.

In a further embodiment, a method is provided for inhibiting an activation of a monoamine receptor comprising contacting the monoamine receptor, or a system containing the monoamine receptor, with the compound of formula (I). The activation of the receptor may be due to an exogenous or endogenous agonist agent, or may be the constitutive activation associated with a native, mutated or modified receptor. The receptor may be purified or present in an in vitro or in vivo system. The receptor may also be present in the central or peripheral nervous system, blood cells or platelets of a non-human or human subject. Also provided are kits for performing the same.

In one embodiment, the compound of formula (I) is selective for 5-HT class serotonin receptors, such as the 5-HT2A subclass of serotonin receptors. In another embodiment, the compound has little or substantially no anti-dopaminergic activity.

One embodiment provides methods of treating a disease condition associated with a monoamine receptor comprising administering to a mammal in need of such treatment an effective amount of the compound of formula (1). One embodiment provides methods for treating or alleviating disease conditions associated with improper function or stimulation of native, as well as mutated or otherwise modified, forms of central serotonin receptors, particularly the 5-HT class of such receptors, comprising administration of an effective amount of a selective inverse agonist of formula (I) to a host in need of such treatment. Also provided are kits for performing the same.

In one embodiment, the receptor is the 5-HT2A subclass. In one embodiment, the disease condition is associated with dysfunction of the serotonin receptor. In another embodiment, the disease condition is associated with activation of the serotonin receptor, for instance, inappropriately elevated or constitutive activation, elevated serotonergic tone, as well as disease conditions associated with secondary cellular functions impaired by such pathologies.

Examples of diseases for which such treatment using the compound of formula (I) is useful include, but are not limited to, neuropsychiatric diseases such as schizophrenia and related idiopathic psychoses, anxiety, sleep disorders, appetite disorders, affective disorders such as major depression, bipolar disorder, and depression with psychotic features, and Tourette's Syndrome, drug-induced psychoses, psychoses secondary to neurodegenerative disorders such as Alzheimer's or Huntington's Disease. It is anticipated that the compound of formula (I), a particularly selective inverse agonist of 5-HT2A that shows little or no activity on dopaminergic receptors, may be especially useful for treating schizophrenia. Treatment using the compound of formula (I) may also be useful in treating migraine, vasospasm, hypertension, various thrombotic conditions including myocardial infarction, thrombotic or ischemic stroke, idiopathic and thrombotic thrombocytopenic purpura, and peripheral vascular disease.

In a further embodiment the present invention provides methods for treating or alleviating a disease condition associated with improper function, dysfunction, or stimulation of native, as well as mutated or otherwise modified, forms of central or peripheral monoamine receptors, such methods comprising administration of an effective amount of a compound of formula (I) to a host in need of such treatment. In one embodiment, the monamine receptor is serotonin receptor in the peripheral nervous system, blood or platelets. In some embodiments, the serotonin receptor is a 5-HT2A subclass receptor. In additional embodiments, the disease condition is associated with increased activity or activation of a serotonin receptor. Also provided are kits for performing the same.

Some embodiments also pertain to the field of predictive medicine in which pharmacogenomics is used for prognostic (predictive) purposes. Pharmacogenomics deals with clinically significant hereditary variations in the response to drugs due to altered drug disposition and abnormal action in affected persons. See e.g., Eichelbaum, *Clin Exp Pharmacol. Physiol.*, 23:983-985 (1996), and Linder, *Clin. Chem.* 43:254-66 (1997). In general, two types of pharmacogenetic conditions can be differentiated: genetic conditions transmitted as a single factor altering the way drugs act on the body (altered drug action), and genetic conditions transmitted as single factors altering the way the body acts on drugs (altered drug metabolism). These pharmacogenetic conditions can occur as naturally occurring polymorphisms.

One pharmacogenomics approach to identifying genes that predict drug response, known as "a genome-wide association," relies primarily on a high-resolution map of the human genome consisting of already known gene-related markers (e.g., a "bi-allelic" gene marker map that consists of 60,000-100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1,000 bases of DNA. A SNP may be involved in a disease process; however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drug's target is known (e.g., a protein or a receptor of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a molecule or modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a molecule or modulator of the invention, such as a modulator identified by one of the exemplary screening assays described herein. As we have described previously, this approach can also be used to identify novel candidate receptor or other genes suitable for further pharmacological characterization in vitro and in vivo.

Accordingly, one embodiment provides methods and kits for identifying a genetic polymorphism predisposing a subject to being responsive to the compound of formula (I). The method comprises administering to a subject an effective amount of the compound; identifying a responsive subject having an ameliorated disease condition associated with a monamine receptor; and identifying a genetic polymorphism in the responsive subject, wherein the genetic polymorphism predisposes a subject to being responsive to the compound. It is anticipated that this method may be useful both for predicting which individuals are responsive to therapeutic effects of the compound and also for predicting those likely to experience adverse side effect responses. This approach may be useful for identifying, for example, polymorphisms in a serotonin receptor that lead to constitutive activation and are thus amenable to inverse agonist therapy. In addition, this method may be useful for identifying polymorphisms that lead to altered drug metabolism whereby toxic byproducts are generated in the body. Such a mechanism has been implicated in the rare, but potentially life threatening side effects of the atypical antipsychotic, clozapine.

In a related embodiment, a method for identifying a subject suitable for treatment with the compound of formula (I) is provided. According to the method, the presence of a polymorphism that predisposes the subject to being responsive to the compound is detected, the presence of the polymorphism indicating that the subject is suitable for treatment. Also provided are kits for performing the same.

The compound of formula (I) preferably shows selective inverse agonist activity towards the 5-HT2A receptor. Such activity is defined by an ability of the ligand to attenuate or abolish the constitutive signaling activity of this receptor. Selectivity in the present context is understood as a property of a compound of the invention whereby an amount of compound that effectively inversely agonizes the 5-HT2A receptor and thereby decreases its activity causes little or no inverse agonistic or antagonistic activity at other, related or unrelated, receptors. In particular, the compound of formula (I) has surprisingly been found not to interact strongly with other serotonin receptors (5-HT 1A, 1B, 1D, 1E, 1F, 2B, 2C, 4A, 6, and 7) at concentrations where the signaling of the 5-HT2A receptor is strongly or completely inhibited. In one embodiment, the compound is also selective with respect to other monoamine-binding receptors, such as the dopaminergic, histaminergic, adrenergic and muscarinic receptors.

One embodiment of the present invention relates to a method of alleviating or treating a disease condition in which modification of monoamine receptor activity, in particular 5-HT2A serotonergic receptor activity, has a beneficial effect by administering a therapeutically effective amount of the compound of formula (I) to a subject in need of such treatment. Such diseases or conditions may, for instance arise from inappropriate stimulation or activation of serotonergic receptors. It is anticipated that by using a compound that is selective for a particular serotonin receptor subtype, in particular 5-HT2A, the problems with adverse side effects observed with the known antipsychotic drugs, such as extrapyramidal effects, may be avoided substantially.

The term "therapeutically effective amount" as used herein means an amount of an active compound or pharmaceutical agent that elicits the biological or medicinal response in a tissue, system, animal or human that is being sought by a researcher, veterinarian, medical doctor or other clinician, which includes alleviation, amelioration, or lessening of the symptoms of the disease being treated, or prevents or slows the progress of the disease or increase of the symptoms.

In one embodiment, the compound of formula (I) may be administered in a single daily dose, or the total daily dosage may be administered in divided doses, for example, two, three or four times daily. Furthermore, the compound of formula (I) may be administered in intranasal form via topical use of suitable intranasal vehicles, via transdermal routes, using those forms of transdermal skin patches well known to persons skilled in the art, by implantable pumps; or by any other suitable means of administration. To be administered in the form of a transdermal delivery system, for example, the dosage administration will, of course, be continuous rather than intermittent throughout the dosage regimen.

The dosage regimen utilizing the compound of formula (I) is selected in accordance with a variety of factors including type, species, age, weight, sex and medical condition of the patient; the severity of the condition to be treated; the route of administration; the renal and hepatic function of the patient; and the particular compound employed. A physician or veterinarian of ordinary skill can readily determine and prescribe the effective amount of the drug required to prevent, counter or arrest the progress of the disease or disorder that is being treated.

For oral administration, compositions containing the compound of formula (I) are preferably provided in the form of tablets containing 0.01, 0.05, 0.1, 0.5, 1.0, 2.5, 5.0, 10.0, 15.0, 25.0 or 50.0 mg of the active ingredient for the symptomatic adjustment of the dosage to the patient to be treated. In one embodiment, a unit dose contains from about 0.001 mg to about 50 mg of the active ingredient. In another embodiment a unit dose contains from about 1 mg to about 10 mg of active ingredient.

The compound of formula (I) may be used alone at appropriate dosages defined by routine testing in order to obtain optimal pharmacological effect on a monoaminergic receptor, in particular the 5-HT2A serotonergic receptor subtype, while minimizing any potential toxic or otherwise unwanted effects. In addition, co-administration or sequential administration of other agents that improve the effect of the compound may, in some cases, be desirable.

In one embodiment, the compound of formula (I) may be combined with an additional therapeutic agent. Additional therapeutic agents may include: levodopa (SINEMET™, SINEMET-CRT™, bromocriptine (PARLODEL™), pergolide (PERMAX™), ephedrine sulfate (EPHEDRINE™), pemoline CYLERT™), mazindol (SANOREX™), d,l-α-methylphenethylamine (ADDERALL™), methylphenydate (RITALIN™), pramipexole (MIRAPEX™), modafinil (PROVIGIL™), ropinirole (REQUIP™), an anti-dyskensia agent, an anti-dystonia, an anti-myoclonus, an anti-tremor agent, or an anti-psychotic agent. In some embodiments, the anti-dyskensia agent is selected from baclofen (Lioresal™), botulinum toxin (Botox™), clonazepam (Klonopin™), or diazepam (Valium™). In some embodiments, the anti-dystonia, anti-myoclonus, or anti-tremor agents are selected from baclofen (LIORESAL™), botulinum toxin (BOTOX™), clonazepam (KLONOPIN™), or diazepam (VALIUM™). In some embodiments, the anti-psychotic agent is selected from chlorpromazine (THORAZINE™), haloperodol (HALDOL™), molindone (MOBAN™), thioridazine (MELLARIL™), a phenothiazine, a butyrophenome, diphenulbutylpiperinde (pimozide), thioxanthines (fluphenthixol), substituted benzamides (sulpiride), sertindole, amisulpride, risperidone, clozapine, olanzapine, ziprasidone, aripiprazole, or their active metabolites (N-desmethylclozapine, N-desmethylolanzapine, 9-OH-risperdone)).

The pharmacological properties and the selectivity of the compound of formula (I) for specific serotonergic receptor subtypes may be demonstrated by a number of different assay methods using recombinant receptor subtypes, preferably of the human receptors if these are available, e.g. conventional second messenger or binding assays. A particularly convenient functional assay system is the receptor selection and amplification assay disclosed in U.S. Pat. No. 5,707,798, which describes a method of screening for bioactive compounds by utilizing the ability of cells transfected with receptor DNA, e.g., coding for the different serotonergic subtypes, to amplify in the presence of a ligand of the receptor. Cell amplification is detected as increased levels of a marker also expressed by the cells.

Treatment of Neuropsychiatric Disorders

In one embodiment, the compound of formula (I) and related serotonin 2A and/or 2C receptor inverse agonists alone or in combination with other antipsychotic drugs, particularly those with dopamine antagonist properties, are used to treat a variety of human neuropsychiatric diseases including schizophrenia, schizoaffective disorders, mania and psychotic depression. Specifically, the compound of formula (I) and related serotonin 2A/2C receptor inverse agonists can improve psychotic symptoms (feelings of being controlled by outside forces, hearing, seeing, smelling or feeling things which are not there, hallucinations and unusual beliefs, delusions). negative symptoms (loss of normal behavior including tiredness, loss of concentration and lack of energy and motivation, and cognitive function in psychotic patients when used alone or in combination with other antipsychotic drugs. These agents also reduce the side-effects associated with the use of existing antipsychotic drugs and reduce the dose of existing agent that is required to achieve antipsychotic efficacy. Specifically, the compound of formula (I) and related compounds alone or in combination with existing antipsychotic drugs can be used to control the behavioral and neuropsychiatric manifestations present in all of these disease states. In some embodiments, pharmaceutical compositions comprised of a combination of the compound of formula (I) and existing antipsychotic agents are used.

Neuropsychiatric disorders associated with psychosis affect a large proportion of the human population. Psychosis appears as a dominating symptom in diverse disorders, including schizophrenia, schizoaffective states, mania, psychotic depression among others. Current treatment options primarily involve pharmacotherapy with a class of drugs known as antipsychotics. Antipsychotics are effective in ameliorating positive symptomotology of these disorders, yet they frequently do not improve and may worsen negative and cognitive symptoms. Significant treatment limiting side effects are common with the use of antipsychotic drugs.

Drugs that possess antipsychotic properties have been in clinical use since the early 1950's. Antipsychotic drugs are widely prescribed to treat psychotic symptoms irrespective of their etiology. Clinical use of these compounds is limited, however, by their side effect profiles. Nearly all of the "typical" or first generation compounds have significant adverse effects on human motor function. These "extrapyramidal" side effects, so termed due to their effects on human motor systems, can be both acute and chronic in nature. Acute effects include dystonic reactions, and a potentially life threatening but rare symptom constellation; neuroleptic malignant syndrome. Chronic side effects include akathisias, tremors, and tardive dyskinesia. Due in large part to these disabling side effects, antipsychotic drug development has been focused on newer "atypical" agents (clozapine, olanzapine, quetiapine, risperidal, arapiprazole) that appear to have reduced liability for inducing adverse motoric effects. These newer "atypical" antipsychotic drugs, however, suffer from other limiting side-effects, including induction of cardiovascular abnormalities, extreme sedation, morbid obesity, type II diabetes, blood dyscrasias and pancreatitis among others.

While the precise molecular mechanisms mediating antipsychotic drug action remain to be elucidated, antipsychotic drugs have been shown, by both in vitro and in vivo methods, to interact with a large number of central monoaminergic neurotransmitter receptors, including dopaminergic, serotonergic, adrenergic, muscarinic, and histaminergic receptors. It is likely that the therapeutic and adverse effects of these drugs are separable and are mediated by distinct receptor subtypes.

Currently, it is thought that antipsychotic drugs reduce the positive symptoms in these disorders by blocking dopamine D2 receptors. This is based on the observation that these all antipsychotic drugs have reasonable affinity for this receptor in vitro, and that a correlation exists between their potency to block D2 receptors and their ability to reduce the positive symptoms of these disorders. Unfortunately, it is likely that antagonism of dopamine D2 receptors also mediates the disabling extrapyramidal side effects.

The only other consistent receptor interaction that these drugs as a class display is inverse agonism of 5-HT2A receptors, suggesting that inverse agonism of these receptors is an alternate molecular mechanism that confers antipsychotic efficacy. This theory is bolstered by a number of basic scientific and clinical observations regarding serotonergic systems and the 5-HT2A receptor in particular (U.S. Pat. No. 6,358, 698 incorporated by reference).

However, nearly all known antipsychotic agents lack specificity in their mechanisms of action. In addition to possessing activity at dopamine D2 receptors and 5-HT2A receptors, these drugs as a class have a multitude of pharmacologically relevant interactions with critical neuronal proteins including a host of cell surface receptors, ion channels, and re-uptake transporters. This lack of drug target specificity likely contributes to the multiplicity of adverse effects associated with use of existing antipsychotic agents.

These observations highlight the need to develop novel therapeutic regimens that are specifically designed to not only demonstrate efficacy against these particular disabling symptoms but to also possess tolerability in these specific patient populations. This can be achieved by improving the selectivity of the drug target interactions of new therapeutic agents. Specifically, the development of agents with novel mechanisms of action that avoid the known pitfalls associated with existing agents is desired. In addition, improved selectivity avoids the known adverse effects associated with interactions with non-efficacy off-target receptor interaction. For example many antipsychotic drugs possess high affinity interactions with H1 receptors. H1 antagonism is associated with sedation. Further, other antipsychotic drugs have affinity interactions with alpha receptors. Antagonism of alpha-1 receptors is associated with orthostasis. Improvements in therapeutic efficacy and safety also can be achieved by combining two or more agents each with selective target interactions to achieve additive or synergistic benefits. Specifically, by combining one drug that specifically interacts with D2 receptors as an antagonist and another drug like the compound of formula (I) that interacts with specifically with 5-HT2A/2C receptors as antagonist or inverse agonist, the multitude of off-target interactions of existing antipsychotic drugs can be avoided.

In one embodiment, serotonin 2A and/or 2C receptor inverse agonists are used to treat a variety of human neuropsychiatric diseases including schizophrenia, schizoaffective disorders, mania, behavioral disturbances associated with dementia and psychotic depression. For example, the compounds disclosed herein have utility in reducing the positive symptoms, improving negative symptoms and enhancing cognitive function in patients with certain neuropsychiatric diseases.

Antipsychotics and dopamine receptor antagonists can be effective in ameliorating positive symptoms in schizophrenia and related diseases. Unfortunately, many of these compounds significantly worsen motor function and increase negative symptoms or leave these and other symptoms untreated in these patients. Biochemical and pharmacological data support the hypothesis that potentiation of serotonergic neurotransmission may be pathophysiologically important in the development of these unwanted effects and conversely blockade of serotonergic neurotransmission may reduced the side-effects associated with antipsychotic drug therapy. While not being bound by this theory, the compound of formula (I) was selected to exploit the relationship of serotonergic activity and the limiting effects associated with antipsychotic therapy.

Haloperidol is a typical antipsychotic with specificity as a D2 receptor antagonist. This compound commonly is used to treat the positive symptoms associated with acute exacerbations of schizophrenia. Unfortunately, the use of this compound is associated with a plethora of unwanted motoric side effects, including akathisia, parkinsonism, tardive dyskinesia and neuroleptic malignant syndrome. This compound also does not alter or worsens negative symptoms and cognitive function in these patients.

In one embodiment, the compound of formula (I) can be used to treat many side-effects that arise from antipsychotic therapy. For example, the compound of formula (I) may be useful for treatment of motoric side-effects of other antipsychotic agents such as haloperidol. In one embodiment, the compound of formula (I) is used for the treatment of motoric side-effects associated with haloperidol treatment.

In one embodiment, the compound of formula (I) may be used prophylactically when for example, it is considered necessary to initiate haloperidol therapy and it is feared that motoric deficits may develop.

In some embodiments, the compound of formula (I) may be used to treat psychosis as a monotherapy or as an adjunct to medicaments to prevent or treat antipsychotic drug side-effects caused by the medicament. Alternatively, the compound of formula (I) may be given in combination with other compounds, which also reduce antipsychotic drug side-effects.

In one embodiment, the compound of formula (I) may used to treat the negative symptoms of certain neuropsychiatric disease including schizophrenia as a monotherapy or as an adjunct to medicaments used to treat the positive symptom of these diseases.

In some embodiments, the compound of formula (I) also may used to improve cognitive function in certain neuropsychiatric disease including schizophrenia as a monotherapy or as an adjunct to medicaments used to treat the positive symptom of these diseases.

Methods of Preparation

The compound of formula (I) may be synthesized by methods described below, or by modification of these methods. Ways of modifying the methodology include, among others, modification in temperature, solvent, reagents, etc.

The first step of the synthesis, illustrated below, is conducted in the presence of acetic acid, $NaBH_3CN$, and methanol to produce the compound of formula (II):

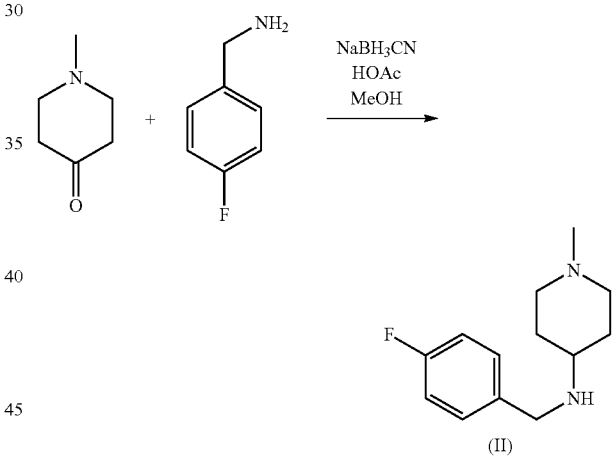

The compound of formula (IV) can be synthesized by treatment of the compound of formula (III) with isobutyl bromide and potassium carbonate in dimethyl formamide (DMF) at about 80° C.:

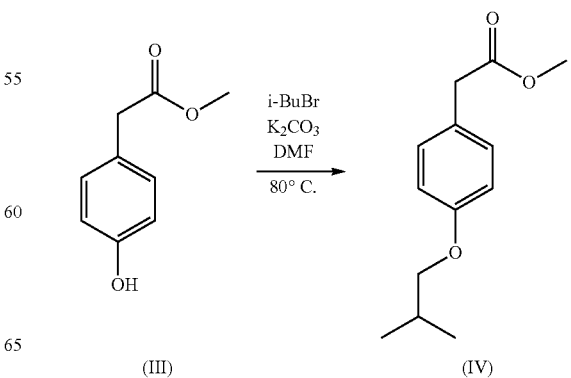

The compound of formula (IV) can be converted to the compound of formula (V) by reaction with potassium hydroxide in methanol/water:

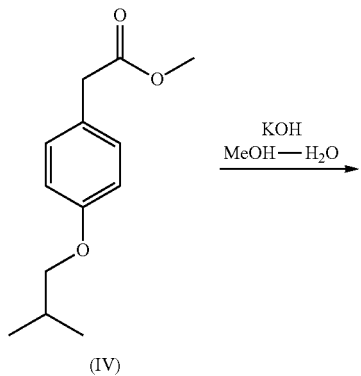

The compound of formula (V) is heated to reflux with diphenylphosphonyl azide (DPPA) and a proton sponge in tetrahydrofuran (THF) to produce the compound of formula (VI):

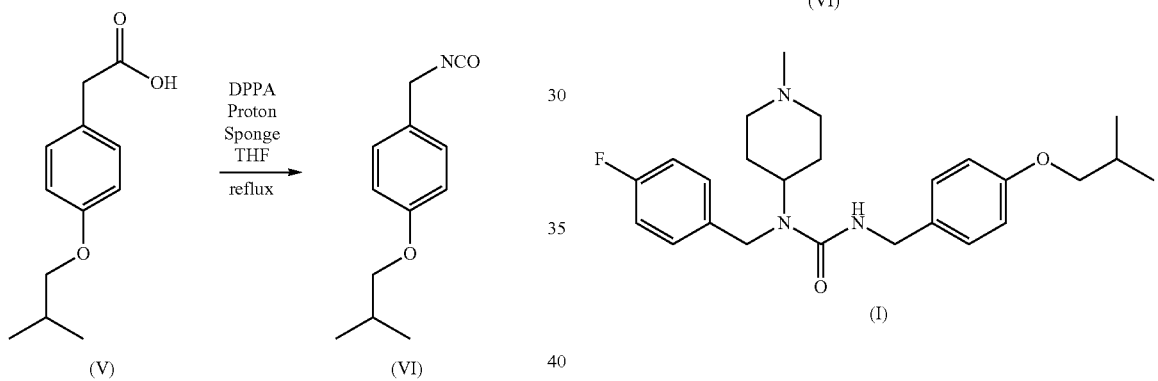

Finally, reaction of the compound of formula (II) with the compound of formula (VI) in methylene chloride produces the compound of formula (I):

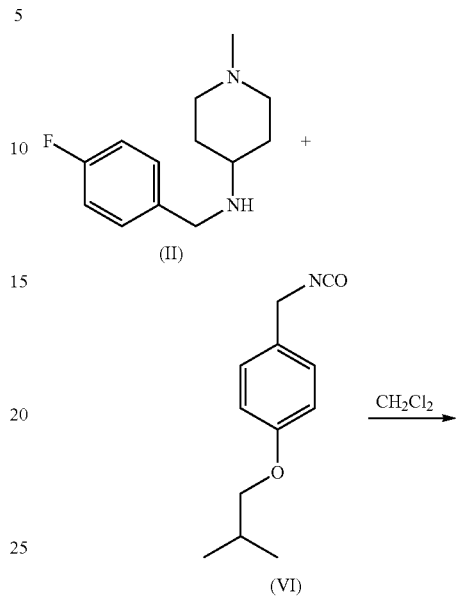

The tartrate salt of the compound of formula (I) may be produced by mixing with L-(+)-Tartaric acid in ethanol:

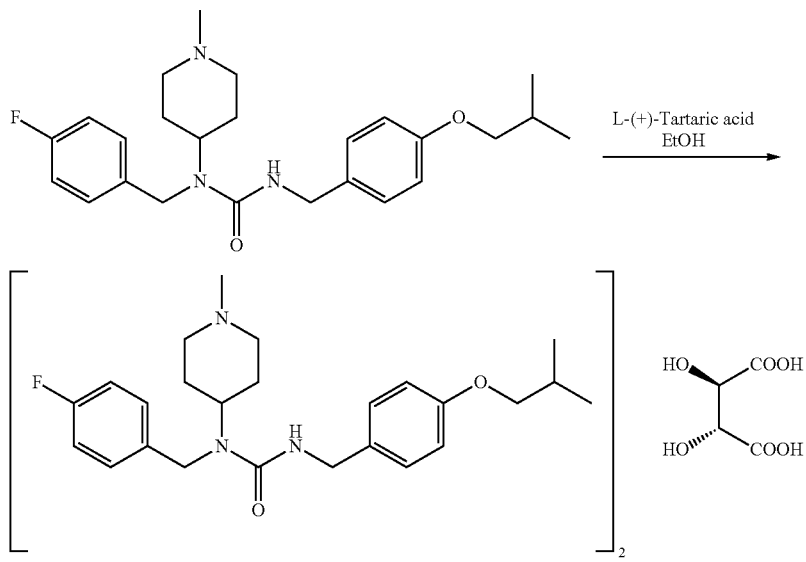

EXAMPLES

The examples below are non-limiting and are set forth to illustrate some of the embodiments disclosed herein.

Example 1

Agonist Studies

Figure 1B:
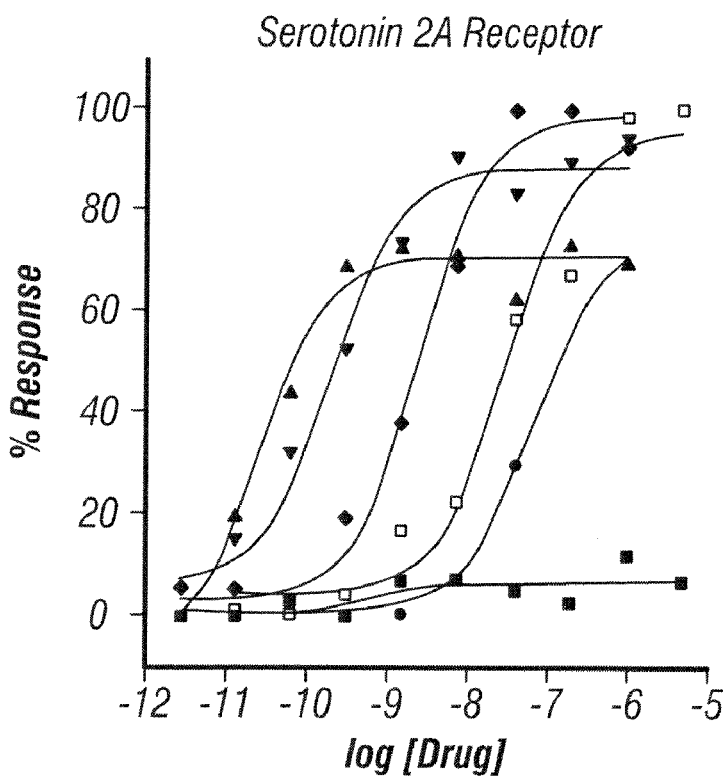
FIG. 1B plots drug activity at human Serotonin 2A receptors.

Parkinson's disease is typically managed using direct acting dopamine agonists. Examples of this class of compounds include pergolide, bromocriptine, pramipexole and ropinirole. These drugs are thought to be effective because of their agonist activity at the dopamine $D_2$, $D_3$, and $D_4$ receptors located in striatal and forebrain regions. This activity may compensate for the progressive loss of forebrain dopaminergic innervation that characterizes the PD. However, these drugs are not specific for these dopaminergic receptors and also possess potent agonist activity at other receptors, including 5HT2A and 5HT2C receptors. Using a physiologically predictive in vitro functional assay, it is shown below that pergolide, lisuride, and bromocriptine display agonist potencies at human 5HT2A receptors that are equivalent to those observed at the human $D_2$ receptor. (FIGS. 1A and 1B, and Table 1).

Using the R-SAT assay, the activity of common dopaminergic compounds against dopamine and serotonin receptor types was studied. (See U.S. Pat. Nos. 5,912,132 and 5,955,281, both of which are hereby incorporated by reference.) In FIG. 1, data were plotted as percentage agonist response as determined for a reference full agonist (100%) versus drug concentration. The reference full agonist used for the $D_2$ receptor was quinpirole, while serotonin was used for the 5HT2A receptor. Compounds tested include dopamine (filled squares), quinpirole (filled circles), lisuride (filled triangles), bromocriptine (filled diamonds), serotonin (open squares), and pergolide (filled inverted triangles). Potencies of representative dose response curves using dopamine $D_2$ receptors were determined and are shown in FIG. 1A; (pergolide-0.21 nM, dopamine-8.0 lisuride-0.023 nM, quinpirole-3.3 nM, bromocriptine-0.43 nM, and serotonin-no response). FIG. 1B shows compound potency against the serotonin 5-HT2A receptor; (dopamine-no response, quinpirole-174 nM, lisuride-0.028 nM, bromocriptine-2.7 nM, serotonin-33 nM, and pergolide-0.22 nM).

Because these drugs are administered in the clinic to achieve $D_2$ receptor occupancy, these data argue that direct acting dopamine agonists are also behaving as 5HT2A receptor agonists in vivo when administered in therapeutic doses to PD patients.

TABLE 1

Serotonin Receptor Agonist Activity of Dopaminergic Agents Used in PD

| Drug | Dopamine D2 | Serotonin 2A | Serotonin 2C |
| --- | --- | --- | --- |
| Dopamine | 8.40 +/− 0.32 | NA | NA |
| Serotonin | NA | 7.73 +/− 0.04 | 7.29 +/− 0.10 |
| Lisuride | 11.00 +/− 0.36 | 10.65 +/− 0.10 | 7.61 +/− 0.13 |
| Pergolide | 9.45 +/− 0.06 | 8.05 +/− 0.22 | 6.66 +/− 0.08 |
| Bromocriptine | 9.30 +/− 0.31 | 8.75 +/− 0.14 | 5.80 +/− 0.05 |
| Ropinirole | 8.19 +/− 0.58 | 6.85 +/− 0.77 | NT |
| Pramipexole | 8.15 +/− 0.38 | 5.93 +/− 0.74 | NT |
| Apomorphine | 6.24 +/− 0.11 | NA | NA |

Data are derived from R-SAT assays. As shown, all compounds displayed full (>75%) relative agonist efficacies. Data are reported as— $Log(EC_{50})$ values+/−standard deviation of three to eight separate determinations. The VGV isoform of the 5HT2C receptor, and the short form of the $D_2$ receptor were utilized for these studies. NA denotes no activity, NT denotes not tested.

The agonist activity of these anti-parkinsonian agents at human 5HT2A/C receptors has particular implications for the generation and treatment of human hallucinations and psychosis. That certain natural and synthetic chemical compounds can induce hallucinatory states in humans has led to detailed investigations of the mechanisms of action of these hallucinogenic or psychotomimetic drugs. These efforts have implicated a number of molecular activities of these classes of drugs as being relevant to their ability to induce hallucinations, particularly visual hallucinations, in normal healthy individuals. Hallucinogens fall into two distinct chemical classes, the phenylethanolamines, and the substituted tryptamines, both of which are structurally related to serotonin. Many in vitro studies, utilizing radioligand binding techniques, as well as functional pharmacological assays, have repeatedly demonstrated that these drugs are potent 5HT2A and 5HT2C receptor agonists (5). More recent in vivo studies, in which normal volunteers are administered the hallucinogen MDMA (Ecstasy) and then evaluated for clinical response, as well as anatomical measures of brain activation utilizing functional neuro-imaging technologies, have demonstrated that the psychometric and pharmacological activities of hallucinogens can be blocked by anti-psychotic drugs as well as the compound ketanserin (6,7). These drugs share a common molecular property, 5HT2A receptor inverse agonism.

Example 2

Inverse Agonist Studies

Once treatment-induced motoric and neuropsychiatric symptoms develop in PD patients, few viable therapeutic options exist to manage these disturbances. Treatment strategies differ for these two classes of symptoms, but one uniformly clinically efficacious, yet poorly tolerated approach, involves the use of antipsychotic agents. Antipsychotics are known to possess high affinity for the dopamine $D_2$ subclass of dopamine receptors and neutral antagonism of these receptors underlie the therapeutic efficacy of these drugs in human psychosis. In addition to dopamine $D_2$ receptor antagonism, these agents possess a wide range of additional potent and pharmacologically relevant activities at many of the other monoaminergic receptor subtypes including serotonin, adrenergic, muscarinic and histaminergic receptors. Of these additional molecular actions, 5HT2A receptor interactions have been the subject of significant study. That antipsychotics have high affinity for multiple receptor subtypes, including serotonin 2 receptors, was demonstrated by the application of radioligand binding techniques (8). The methodologies used to document this cannot define the nature of the interaction between an anti-psychotic antipsychotic and a given receptor. For example, the methods are unable to distinguish as to whether a drug possesses positive (agonist) or negative (inverse agonist) intrinsic activity, or if it lacks intrinsic activity and functions as a neutral antagonist. Recently, this class of drugs was profiled using a functional assay that can discriminate the mechanistic nature of a drug-target interaction (9).

This approach revealed a number of novel aspects of antipsychotic drug action (See U.S. Pat. No. 6,358,698, which is hereby incorporated by reference in its entirety). It confirmed that these drugs as a class possess potent neutral antagonistic activity at the $D_2$ receptor. Importantly, it also revealed that nearly all antipsychotic drugs, with the exception of the substituted benzamides, possess potent negative intrinsic activity (inverse agonism) at the 5HT2A receptor. These efforts have identified inverse agonist activity at the 5HT2A receptor as being a critical molecular component of anti-psychotic drug action, and suggest that compounds that are selective 5HT2A receptor inverse agonists may have antipsychotic efficacy, even in the absence of $D_2$ receptor activity.

None of the older typical antipsychotics, exemplified by haloperidol, can be administered to PD patients because of severe worsening in their motor states. The more recent development of newer atypical agents, namely those with reduced (but clearly not absent) liability to induced motoric side effects, suggested that perhaps these agents could be used in PD patients to control dyskinesias and hallucinosis. Unfortunately, the majority of these agents are not tolerated in PD patients secondary to worsening of motor function (10). Of the atypical agents, only one, clozapine, has shown efficacy in treating these adverse treatment-induced side effects in PD patients without untoward motoric liabilities. As such, an improved understanding of the in vitro molecular profile of clozapine can provide critical insights into the design of novel agents for these difficult to treat indications.

efficacy in this indication. Detailed functional profiling of clozapine against over 30 of the known monoaminergic receptor subtypes has identified only five sites with higher affinity than dopamine $D_2$ receptors, histamine $H_1$, muscarinic m1 and m4, and serotonin 2A, 2B, and 6 receptors. Table 2 reports the absolute and relative potencies of clozapine at some of these monoamine receptor targets as determined by the physiologically predictive in vitro R-SAT assay. These data suggest that at the clinical dosing and serum levels of clozapine observed in PD, two receptor sites are preferentially occupied, the histamine $H_1$ and 5HT2A receptors.

Conversely, plasma levels achieved with 50 mgs/day of clozapine result in full occupancy of cortical 5HT2A receptors, and extrapolation to the plasma levels observed in PD patients treated for psychosis suggest near complete occupancy of 5HT2A receptors at these dosages as well (16). Whereas central occupancy of 5HT2A receptors, coupled with negative intrinsic activity, may mediate efficacy in these states, central occupancy of histamine $H_1$ receptors is known to cause sedation, an effect that was observed in the majority of PD patients treated with low dose clozapine. Taken together these data suggest that clozapine is acting primarily as a 5HT2A receptor inverse agonist in this clinical setting.

TABLE 2

Antagonist and Inverse Agonist Potencies of Clozapine at Monoamine Receptors

| | $D_2$ | 5HT2A | 5HT2B | 5HT2C | $H_1$ |
|---|---|---|---|---|---|
| Clozapine | 72 +/− 56 | 6.4 +/− 1.0 | 20 +/− 9 | 250 +/− 60 | 0.40 +/− 0.07 |
| Ratio to $D_2$ | | 11 | 3.6 | 0.3 | 180 |

The demonstration that clozapine is tolerated in PD patients comes from studies on treatment-induced psychosis. Two well-designed placebo controlled, double blind clinical trials have shown that clozapine is efficacious in psychotic PD patients, and does not worsen parkinsonism, at doses in the 25-35 mg/day range (11,12). Similarly, two open label studies of clozapine in L-dopa and apomorphine induced dyskinesias also demonstrate efficacy and tolerability of low doses of clozapine, on the order of 50-100 mgs/day in these patients (13,14). The dosages used in these PD patients are much lower than the typical 600-900 mg/day range of doses used in treatment refractory schizophrenia. Commensurate with this lower dosing, plasma levels of clozapine in PD patients with psychosis ranged from 4.5 to 16.1 ng/ml (15). This is dramatically lower than the $\geq 250$ ng/ml average serum levels that are associated with therapeutic response in refractory schizophrenic patients.

Not surprisingly, the administration of low dose clozapine, and the commensurate plasma levels obtained at these doses, are well below those necessary for $D_2$ receptor occupancy, providing a mechanistic understanding of why these dosages are tolerated with respect to motoric liability in these patients. (Positron emission tomography (PET) studies in schizophrenic patients have defined steady state plasma concentrations of clozapine that are required to generate high occupancy of striatal dopamine $D_2$ receptors). These data also argue that efficacy in dyskinesia and psychosis is mediated by one or more of the non-$D_2$ receptor targets of this drug. Since rank orders of receptor potencies, as determined by in vitro pharmacological assays, has repeatedly been shown to be a reliable predictor of in vivo receptor action, the receptor sites for which clozapine display a higher potency than $D_2$ receptors would be predicted to potentially mediate its clinical Data are derived from (9) and are reported as Ki values for the D2 receptor determined as a competitive antagonist, and $EC_{50}$ values for the remaining receptors determined as inverse agonists, in nanomolar unit's+/−standard deviation of three to eight separate determinations.

Behavioral Pharmacological Evidence

The tartrate salt of the compound, N-(1-methylpiperidin-4-yl)-N-(4-fluorophenylmethyl)-N'-(4-(2-methylpropyloxy)phenylmethyl)carbamide (compound of formula (I)), is a potent, selective, orally bioavailable 5HT2A receptor inverse agonist. The compound of formula (I) also possesses lesser potency as a 5-HT2C receptor inverse agonist and lacks intrinsic activity at the remaining monoaminergic receptor subtypes. Perhaps most notably, the compound of formula (I) lacks activity at dopamine receptor subtypes. (See U.S. patent application Ser. No. 09/800,096, which is hereby incorporated by reference in its entirety). Extensive behavioral pharmacological profiling of this agent, including pre-clinical models of antipsychotic and anti-dyskinetic drug actions support the therapeutic use of the compound of formula (I) in Parkinson's Disease and related human neurodegenerative diseases.

Example 3

Animal Studies

To determine potential in vivo antipsychotic activity, we studied the compound of formula (I) in an animal model that predicts such efficacy in humans. The compound of formula (I) attenuates hyperactivity induced by the non-competitive N-methyl-d-aspartate (NMDA) antagonist MK-801 (dizocilpine) with a minimum effective dose of 1 mg/kg s.c. (FIG.

Figure 2A:
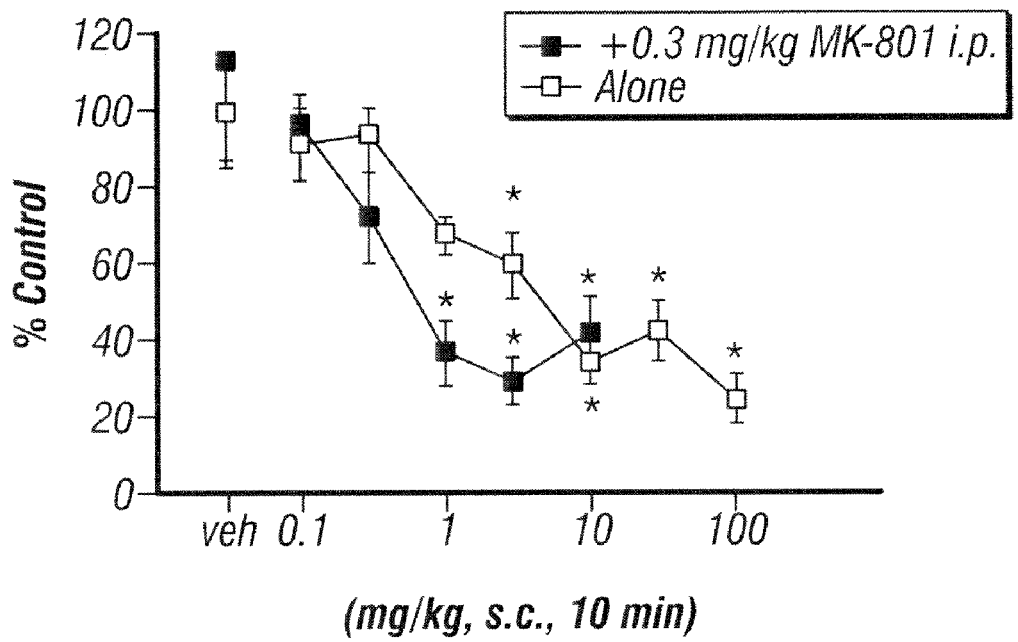
FIG. 2A is a plot of the efficacy of the compound of formula (I) in reducing MK-801 induced locomotor behaviors in rats against a control after s.c. administration over a ten (10) minute time period.
Figure 2B:
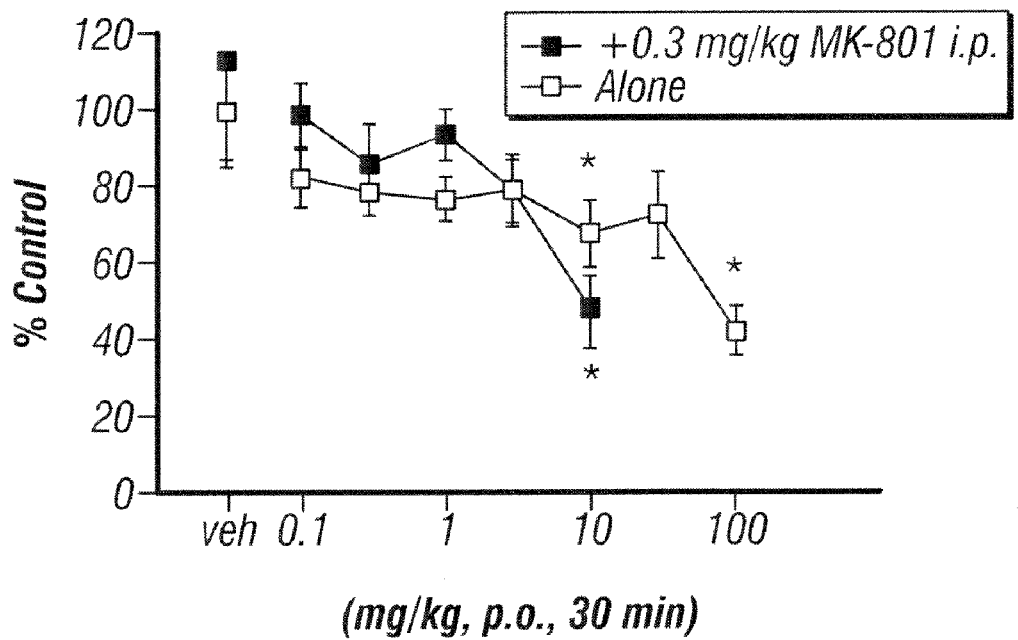
FIG. 2B is a plot of the efficacy of the compound of formula (I) in reducing MK-801 induced locomotor behaviors in rats against a control after oral administration over a thirty (30) minute time period.

2A), and 10 mg/kg p.o. (FIG. 2B). The compound of formula (I) also reduced spontaneous locomotion at 3 mg/kg and higher s.c. doses (FIG. 2A), and at oral doses between 10 and 100 mg/kg (FIG. 2B). In FIGS. 2A and 2B, asterisks indicate statistical significance (p<0.05) compared to respective vehicle control. Inhibition of MK-801 is a property shared by most atypical antipsychotic agents, and after i.p. administration, the compound of formula (I) attenuated MK-801 hyperactivity at 1 mg/kg, in a manner similar to the atypical antipsychotic clozapine.

Example 4

Primate Animal Studies

Figure 3:
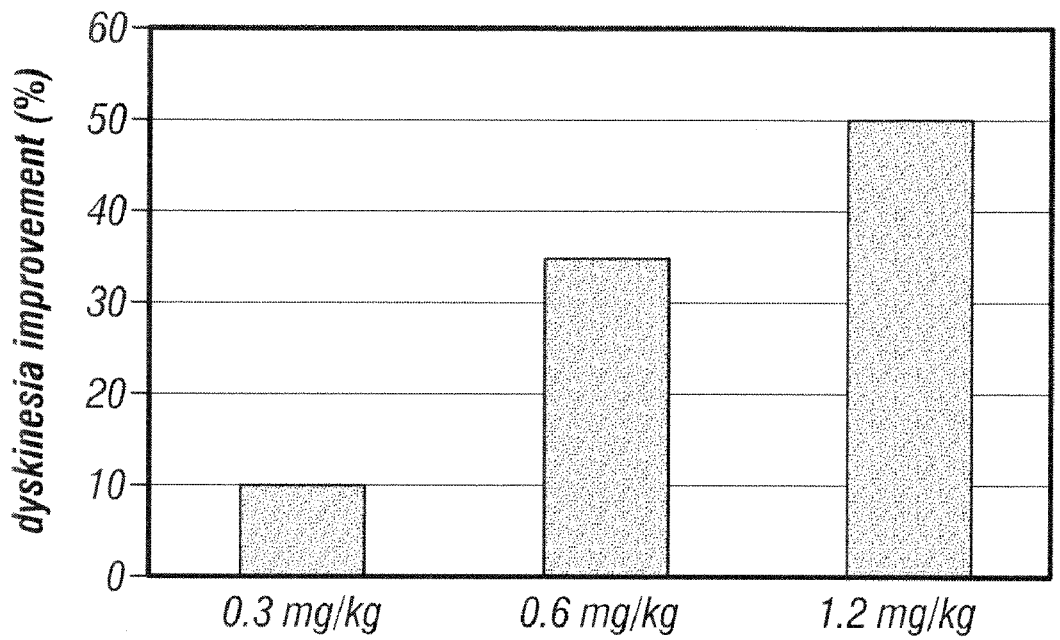
FIG. 3 shows a bar graph that indicates three dosage levels of the compound of formula (I) and the effect of each dosage on reducing dyskinesia in a primate model.

To determine the potential in vivo anti-dyskinetic activity, we studied the compound of formula (I) in an animal model that predicts such efficacy in humans. The use of 1-methyl-4-phenyl-1,2,3,6-tetrahydropyrilidine (MPTP) to induce parkinsonism in monkeys, coupled with prolonged administration of L-dopa induces severe dyskinesias. The compound of formula (I), when administered s.c., to dyskinetic primates was found to significantly diminish L-dopa induced dyskinesias in a dose dependent manner as determined by the reduction of observable dyskinetic movements scored as a percentage of those present in placebo injected animals (FIG. 3).

Example 5

5HT2A/C Serotonin Antagonist Treatment of Parkinson's Disease

The present example demonstrates that blockage of 5HT2A/C receptors with the compound of formula (I) in parkinsonian patients reduces levodopa-associated dyskinesias and motor response fluctuations. Additionally, the compound of formula (I) is shown to be safe and tolerated at effective doses and potentiates the beneficial effects of levodopa on parkinsonian symptoms.

The compound of formula (I) is administered orally in a group of 21 parkinsonian patients in a double blind, placebo controlled study lasting approximately 5 weeks. An unbalanced parallel-group dose escalation design is used involving an initial placebo run-in, followed by a randomized (active) phase of the compound of formula (I) or placebo. The compound of formula (I) is administered once daily for four weeks, with the dose escalating once each week. Assessments are made on the first day of each dose escalation.

The study is conducted on an outpatient basis. Studies of the compound of formula (I) effect on the motor response to levodopa are conducted in accordance with the standard Experimental Therapeutics Branch (ETB) paradigm, which makes use of a steady state infusion of dopaminomimetics in order to maximize the reliability of data acquisition as well as to permit determination of the anti-parkinsonian efficacy half-time.

Patients who participate in the study have particular characteristics. The patients are between 30 and 80 years of age, inclusively. The patients had been diagnosed with idiopathic Parkinson's disease based on the presence of a characteristic clinical history and neurological findings. The patients displayed relatively advanced disease symptoms with levodopa-associated motor response complications, including peak-dose dyskinesias and wearing-off fluctuations.

The sample size is calculated for the primary endpoint: the Unified Parkinson's Disease Rating Scale (UPDRS) part 111 motor examination. A sample size of 17 provides 80% power to detect predicted differences, a 40% reduction, with a standardized effect size of 1, using a two-tailed t-test at the 0.05 significance. This assumes an anti-dyskinetic effect of the compound of formula (I) to be compared to that of amantadine (as observed in previous ETB studies), and a linear dose-response of the compound of formula (I). In this phase 2 study we will accept a two-sided alpha at a 0.05 significance level. Four patients will be added for the placebo group, totaling 21 subjects enrolled in the study.

Patients enter the levodopa infusion optimal rate determination (dose finding) portion of the study as soon as all prohibited medication has been withdrawn for at least four weeks. If the patient has had an intravenous dosing rate for levodopa optimized within the past three months, these doses may be used for the study.

Intravenous infusion of levodopa is conducted in an in-patient ward. On the night prior to all infusions, subjects' usual anti-parkinsonian medications are withheld (levodopa by 12 AM, dopamine agonists by 6 PM). During the first and second days of optimal rate determination, two baseline UPDRS ratings are performed prior to levodopa infusion. Initially, the "optimal" rate of levodopa infusion is carefully titrated for each individual to determine the minimum dose needed to achieve a stable "on" state characterized by an "optimal" reduction in parkinsonian signs and mild but ratable dyskinesias (comparable to patient's usual "on" state). Dyskinesia severity is similar to that experienced with each patient's usual therapeutic regimen. Levodopa will be administered by means of an indwelling intravenous catheter. The initial infusion rate of levodopa will not exceed 80 mg/hr. Subsequent infusion rates may be gradually increased until the optimal rate is found, up to a maximum of 2 mg/kg/hour.

Levodopa infusions will ordinarily last up to 8 hours, but may be continued uninterrupted for several days or be repeated on other days to obtain reliable assessment of motor function. The peripheral decarboxylase inhibitor carbidopa (50 mg, given every 3 hours) is administered orally starting at least one hour prior to intravenous administration of levodopa and continuing until levodopa effects have worn off. After the initial "optimal" rate finding for levodopa infusion, all subsequent infusions are given at the predetermined "optimal rate". As an intravenous levodopa formulation is not commercially available in this country, is administered under ETB IND 22,663.

Patients are dosed according to Table 3:

TABLE 3

| Patient group | Week 1 | Week 2 | Week 3 | Week 4 | Week 5 |
| --- | --- | --- | --- | --- | --- |
| I | Placebo | Placebo | Placebo | Placebo | Placebo |
| II | Placebo | 30 mg Compound (I) | 70 mg Compound (I) | 150 mg Compound (I) | 300 mg Compound (I) |

Patients proceed through this dose escalation scheme until week 5 or until maximum tolerated dose is attained.

Throughout the study, patients are evaluated weekly for drug safety and tolerability during their inpatient admission and two weeks after treatment for an outpatient follow-up visit. During each inpatient admission, patients remain under close medical monitoring by staff physicians and nurses. If at any time during the treatment period, the staff physician determines that a patient does not tolerate any given dose, the patient will be considered to have attained maximum tolerated dose and will not receive any additional doses of the compound of formula (I). Patients are encouraged to contact study staff between study days to report any adverse experiences.

Patients are observed in the hospital and will not be discharged until free of all significant adverse effects, if any. Safety assessments, which are performed on study days, include adverse experiences, monitoring vital signs, standard safety monitoring, and cardiac monitoring.

Subjects in Patient Group II show a reducing in levodopa-associated dyskinesias and motor response fluctuations. The subjects in Patient Group II tolerate the compound of formula (I) at all doses administered. The compound of formula (I) therapy also potentiates the beneficial effects of levodopa on parkinsonian symptoms.

Example 6

R-SAT Assay

The functional receptor assay Receptor Selection and Amplification Technology (R-SAT) was used to investigate the activity of the compound of formula (I) as an inverse agonist at 5HT2A receptors. The compound of formula (I) exhibited high potency (pIC50 of 9.1) and high efficacy (98%) at 5HT2A receptors.

Example 7

Anti-Psychotic Activity Study

Figure 4:
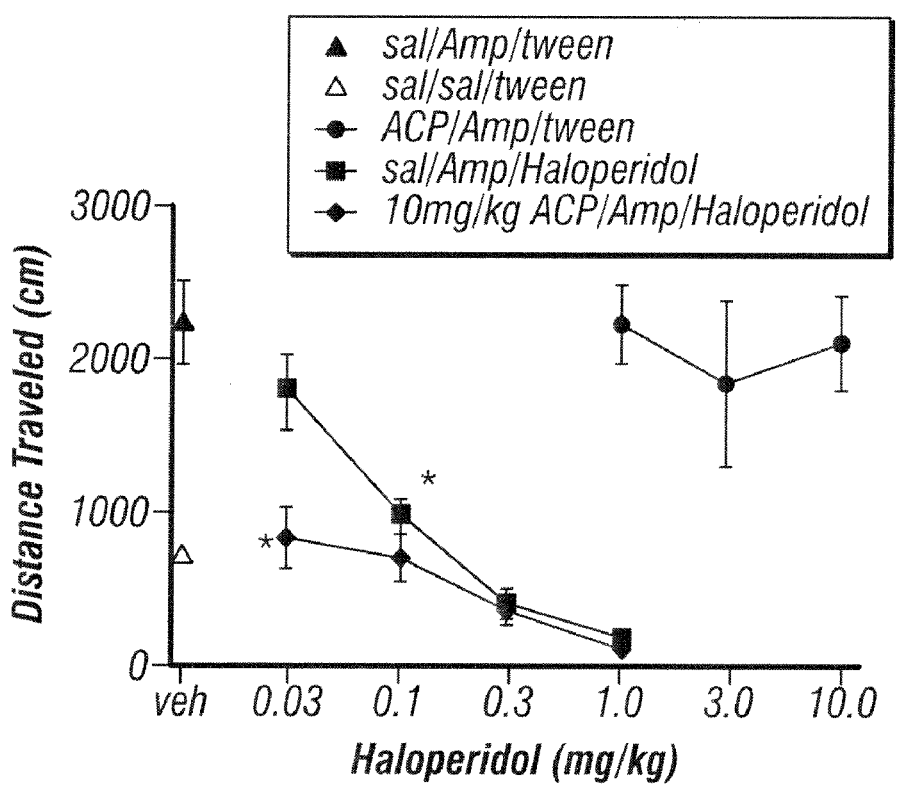
FIG. 4 shows the affect of the compound of formula (I) on amphetamine induced hyperactivity in mice when used in combination with varying doses of Haloperidol.

To determine potential in vivo antipsychotic activity, we studied the compound of formula (I) in an animal model that predicts such efficacy against positive symptoms in humans (FIG. 4). In FIG. 4, ACP refers to the compound of formula (I). The compound of formula (I) did not reduce hyperactivity induced by 3.0 mg/kg I.P. of the indirect dopamine agonist d-amphetamine when administered alone at doses of 10.0 mg/kg P.O. and below to mice. As expected, haloperidol dose-dependently reduced amphetamine hyperactivity with a minimally significant effect seen at 0.1 mg/kg, s.c. When a 10.0 mg/kg P.O. dose of the compound of formula (I) was administered in combination with various s.c. doses of haloperidol, the minimally significant dose of haloperidol was decreased to 0.03 mg/kg. With this combination, amphetamine hyperactivity is completely reversed. Thus, an inactive dose of the compound of formula (I), when combined with an inactive dose of haloperidol produces a complete reversal of amphetamine hyperactivity. This suggests that the antipsychotic activity of haloperidol may be significantly enhanced when it is combined with the compound of formula (I). Equally important, when the compound of formula (I) is combined with haloperidol, the dose of haloperidol can be lowered without a loss of efficacy. This would be expected to improve the safety margin for the clinical use of haloperidol in neuropsychiatric diseases.

LITERATURE CITED

The following references are incorporated herein by reference in their entireties.
1. Everett, G., M., and Borcherding, J., W. (1970) L-dopa: effect on concentration of dopamine, norepinephrine and serotonin in brains of mice. *Nature*, 168: 849-850.
2. Butcher, L., Engel, J., and Fuxe, K. (1970) L-dopa induced changes in central monoamine neurons after peripheral decarboxylase inhibition. *J. Pharm. Pharmac.*, 22: 313-316.
3. NG, K., Y., Chase, T., N., Colburn, R., W., and Kopin, I., J. (1970) L-dopa induced release of cerebral monoamines. *Science*. 170: 76-77.
4. Birkmayer. W., Danielezyk. W., Neumayer, E., and Riederer, P. (1974) Nucleus Ruber and L-dopa Psychosis: Biochemical Post mortem findings. *Journal of Neural Transmission*, 35: 93-116.
5. Sadzot, B., Baraban, J., M., Glennon, R., A., Lyon, R., A., Leonhardt, S., Jan, C., R., and Tietler, M. (1989) Hallucinogenic drug interactions at human brain 5-HT2 receptors; implications for treating LSD-induced hallucinogenesis. *Psychopharmacology*, 98(4): 495-499.
6. Liechti, M., E., Geyer, M., A., Hell, D., and Vollenwieder, F., X. (2001) Effects of MDMA (ecstasy) on prepulse inhibition and habituation of startle in humans after pretreatment with citalopram, haloperidol, or ketanserin., *Neuropsychopharmacology*, 24(3): 240-252.
7. Gamma, A., Buck, A., Berthold, T., Liechti, M., E., and Vollenweider, F., X. (2000) 3,4-methylenedioxymethamphetamine (MDMA) modulates cortical and limbic brain activity as measured by [H(2)(15)O]-PET in healthy humans., *Neuropsychopharmacology*, 23(4): 388-395
8. Leysen, J., E., Niemegeers, C., J., Tollenaraere, J., P., and Laduron, P., M. (1978) Serotonergic component of neuroleptic receptors. *Nature* (Lond) 272: 168-171.
9. Weiner, D., M., Burstein, E., S., Nash, N., Croston, G., E., Currier, E., A., Vanover, K., E., Harvey, S., C., Donohue, E., Hansen, H., C., Andersson, C., M., Spalding, T., A., Gibson, D., F., Krebs-Thomson, K., Powell, S., B., Geyer, M., A., Hacksell, U., and Brann, M., R. (2001) 5-hydroxytryptamine 2A receptor inverse agonists as antipsychotics. *J Pharmacol Exp Ther.* 299(1): 268-76.
10. Friedman, J., K. and Factor, S., A. (2000) Atypical antipsychotics in the treatment of drug-induced psychosis in Parkinson's disease. *Mov. Disord,* 15(2): 201-211.
11. The Parkinson Study Group (1999) Low-dose clozapine for the treatment of drug-induced psychosis in Parkinson's disease. *New Eng. J. Med.,* 340(10): 757-763.
12. The French Clozapine Study Group (1999) Clozapine in drug-induced psychosis in Parkinson's disease. *Lancet,* 353: 2041-2042.
13. Bennett, J., P., Landow, E., R., and Shuh, L., A. (1993) Suppression of dyskinesias in advanced Parkinson's Disease. II Increasing daily clozapine doses suppress dyskinesias and improve parkinsonism symptoms. *Neurology,* 43: 1551-1555.
14. Durif, F., Vidailhet, M., Assal, F., Roche, C., Bonnet, A., M., and Agid, Y. (1997) Low-dose clozapine improves dyskinesias in Parkinson's disease. *Neurology,* 48: 658-662.
15. Meltzer, H., Y., Kennedy, J., Dai, J., Parsa, M., and Riley, D. (1995) Plasma clozapine levels and the treatment of L-DOPA-induced psychosis in Parkinson's disease. A high potency effect of clozapine. *Neuropsychopharmacology,* 12(1): 39-45.
16. Nordstrom, A., L., Farde, L., and Halldin, C. (1993) High 5-HT2 receptor occupancy in clozapine treated patients as demonstrated by PET. *Psychopharmacology,* 110(3): 365-367.
17. Bibbiani, F., Oh, F., D., and Chase, T., C. (2001) Serotonin 5-HT1A agonist improves motor complications in rodent and primate parkinsonian models. *Neurology,* 57: 1829-1834.

What is claimed is:

1. A method of treating bipolar disorder in a patient, comprising administering to a patient in need of such treatment a therapeutically effective amount of a compound of formula (I):

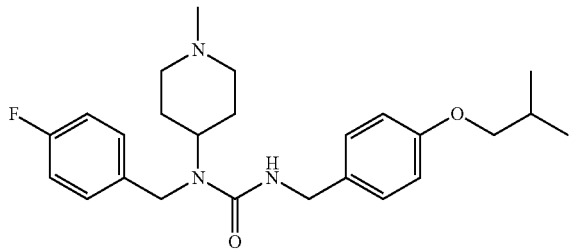

or a pharmaceutically acceptable salt thereof.

2. The method of claim 1, wherein the salt is a tartrate salt.

3. The method of claim 1, wherein the amount of the compound of formula (I), or a pharmaceutically acceptable salt thereof, is from about 0.001 mg to about 50 mg.

4. The method of claim 1, wherein the amount of the compound of formula (I), or a pharmaceutically acceptable salt thereof, is from about 1 mg to about 10 mg.

5. The method of claim 1, wherein the amount of the compound of formula (I), or a pharmaceutically acceptable salt thereof, is about 10 mg.

6. The method of claim 1, wherein the amount of the compound of formula (I), or a pharmaceutically acceptable salt thereof, is about 25 mg.

7. The method of claim 1, wherein the amount of the compound of formula (I), or a pharmaceutically acceptable salt thereof, is about 50 mg.

8. The method of claim 1, wherein the compound of formula (I) is administered daily.

9. The method of claim 1, wherein the compound of formula (I) is administered once daily.

10. The method of claim 1, wherein the compound is administered in combination with an anti-psychotic agent.

11. The method of claim 10, wherein the anti-psychotic agent selected from the group consisting of chloropromazine, haloperidol, molindone, thioridazine, a phenothiazine, a butyrophenone, diphenylbutylpiperidine, a thioxanthine, fluphenthixol, a substituted benzamide, sulpiride, sertindole, amisulpride, risperidone, clozapine, olanzapine, ziprasidone, aripirazole, N-desmethylclozapine, N-desmethylolanzapine, and 9-OH-risperidone.

12. The method of claim 10, wherein the anti-psychotic agent is haloperidol or risperidone.

* * * * *